(12) United States Patent
D'Andrade et al.

(10) Patent No.: US 10,279,216 B2
(45) Date of Patent: May 7, 2019

(54) EXERCISE TRAINING SYSTEM

(71) Applicant: FITLIGHT SPORTS CORP., Aurora (CA)

(72) Inventors: Derek D'Andrade, King (CA); Dennis Pedersen, Aarhus (DK); Erik Vege Rasmussen, Risskov (DK)

(73) Assignee: FITLIGHT SPORTS CORP., Aurora (CA)

( * ) Notice: Subject to any disclaimer, the term of this patent is extended or adjusted under 35 U.S.C. 154(b) by 0 days.

(21) Appl. No.: 15/805,587

(22) Filed: Nov. 7, 2017

(65) Prior Publication Data

US 2018/0214744 A1  Aug. 2, 2018

Related U.S. Application Data

(63) Continuation of application No. 14/356,448, filed as application No. PCT/CA2012/001048 on Nov. 15, 2012, now Pat. No. 9,808,671.

(Continued)

(51) Int. Cl.
*A63B 24/00* (2006.01)
*A63B 69/00* (2006.01)
(Continued)

(52) U.S. Cl.
CPC .......... *A63B 24/0087* (2013.01); *A61B 5/162* (2013.01); *A63B 24/0021* (2013.01);
(Continued)

(58) Field of Classification Search
CPC .............. A63B 2220/53; A63B 69/004; A63B 24/0062; A63B 2220/801; A61B 5/162; A61B 5/103; G09B 19/003
(Continued)

(56) References Cited

U.S. PATENT DOCUMENTS 5,812,239 A   9/1998 Eger
6,093,160 A   7/2000 Augustine
(Continued)

FOREIGN PATENT DOCUMENTS

CA   1203258 A1   4/1986
CA   2536020 A1   8/2007
(Continued)

OTHER PUBLICATIONS

Ludvigsen, et al., "TacTowers: An Interactive Training Equipment for Elite Athletes", DIS 2010, Aug. 16, 2010, pp. 112-415, Aarhus, Denmark.

(Continued)

*Primary Examiner* — Jack Yip
(74) *Attorney, Agent, or Firm* — Millman IP Inc.

(57) ABSTRACT

An exercise training system is provided having a system controller and a plurality of stimulant target units connected via a wireless network to the system controller. Each stimulant target unit has a light source providing light to stimulate a user, a proximity sensor providing an output of a distance between the proximity sensor and an object external to the unit, and means for providing feedback to the user to signal that the unit has been actuated by the user. The system controller includes a program for activating the stimulant target units in a sequence. The reaction by the user to the illumination is registered when the user brings a body part or other object to within a selected distance of the proximity sensor, this distance being programmable by the user.

9 Claims, 35 Drawing Sheets

Related U.S. Application Data

(60) Provisional application No. 61/559,940, filed on Nov. 15, 2011.

(51) Int. Cl.
| | | |
|---|---|---|
| *A63B 71/06* | (2006.01) | |
| *G08B 5/36* | (2006.01) | |
| *H04B 10/114* | (2013.01) | |
| *A61B 5/16* | (2006.01) | |
| *G09B 19/00* | (2006.01) | |
| *A63B 23/02* | (2006.01) | |
| *A63B 22/00* | (2006.01) | |
| *A63B 102/06* | (2015.01) | |
| *A63B 102/02* | (2015.01) | |
| *A63B 21/00* | (2006.01) | |
| *A63B 102/22* | (2015.01) | |

(52) U.S. Cl.
CPC ...... *A63B 69/0053* (2013.01); *A63B 71/0622* (2013.01); *G08B 5/36* (2013.01); *H04B 10/1143* (2013.01); *A61B 2505/09* (2013.01); *A63B 21/4029* (2015.10); *A63B 23/0211* (2013.01); *A63B 2022/0092* (2013.01); *A63B 2024/0037* (2013.01); *A63B 2102/02* (2015.10); *A63B 2102/06* (2015.10); *A63B 2102/22* (2015.10); *A63B 2209/10* (2013.01); *A63B 2220/40* (2013.01); *A63B 2220/53* (2013.01); *A63B 2220/801* (2013.01); *A63B 2220/805* (2013.01); *A63B 2225/50* (2013.01); *A63B 2225/54* (2013.01); *A63B 2243/007* (2013.01); *A63B 2243/0025* (2013.01); *A63B 2243/0033* (2013.01); *A63B 2243/0095* (2013.01); *A63B 2244/10* (2013.01); *G09B 19/0038* (2013.01)

(58) Field of Classification Search
USPC .................. 482/8, 84, 83; 473/422; 434/247
See application file for complete search history.

(56) References Cited

U.S. PATENT DOCUMENTS

| | | |
|---|---|---|
| 6,430,997 B1 | 8/2002 | French et al. |
| 7,192,387 B2 | 3/2007 | Mendel |
| 7,981,009 B2 | 7/2011 | Brenner et al. |
| 8,777,818 B1 | 7/2014 | Tate, Jr. |
| 2002/0103024 A1 | 8/2002 | Jeffway, Jr. |
| 2003/0085870 A1 | 5/2003 | Hinckley |
| 2005/0065452 A1 | 3/2005 | Thompson |
| 2005/0167907 A1 | 8/2005 | Curkendall et al. |
| 2006/0089213 A1 | 4/2006 | Snyder |
| 2008/0102991 A1* | 5/2008 | Hawkins ............ A63B 69/0053 473/422 |
| 2008/0125288 A1 | 5/2008 | Case |
| 2008/0176665 A1 | 7/2008 | Snyders |
| 2008/0261727 A1 | 10/2008 | Snyder |
| 2009/0264262 A1 | 10/2009 | Brenner et al. |
| 2010/0296285 A1 | 11/2010 | Chemel |
| 2010/0324443 A1 | 12/2010 | Ashton-Miller et al. |
| 2012/0302301 A1* | 11/2012 | Homsi ............... A63B 24/0021 463/2 |

FOREIGN PATENT DOCUMENTS

| | | |
|---|---|---|
| EP | 0403130 A1 | 12/1990 |
| GB | 2270004 A | 3/1994 |
| JP | 11253502 A | 9/1999 |
| JP | 2010253236 A | 11/2010 |
| WO | 2006053000 A2 | 5/2006 |
| WO | 2007060401 A1 | 5/2007 |
| WO | 2007142588 A1 | 12/2007 |

OTHER PUBLICATIONS

Bech, Rasmus, "Erik Roads have been to mastermind: 'Best invention since the ball'", Politiken Newspaper, Dec. 2, 2013, Politiken.dk.

EP12849537.1, Communication pursuant to Rule 114(2) EPC, Aug. 12, 2014.

Fitlight Webpage Inventor Bio, http://www.fitlighttraining.com/fitlight.aspx, date unknown, FitLight.

"Erik Roads have invented new training system", http://www.opfind.nu, date unknown.

* cited by examiner

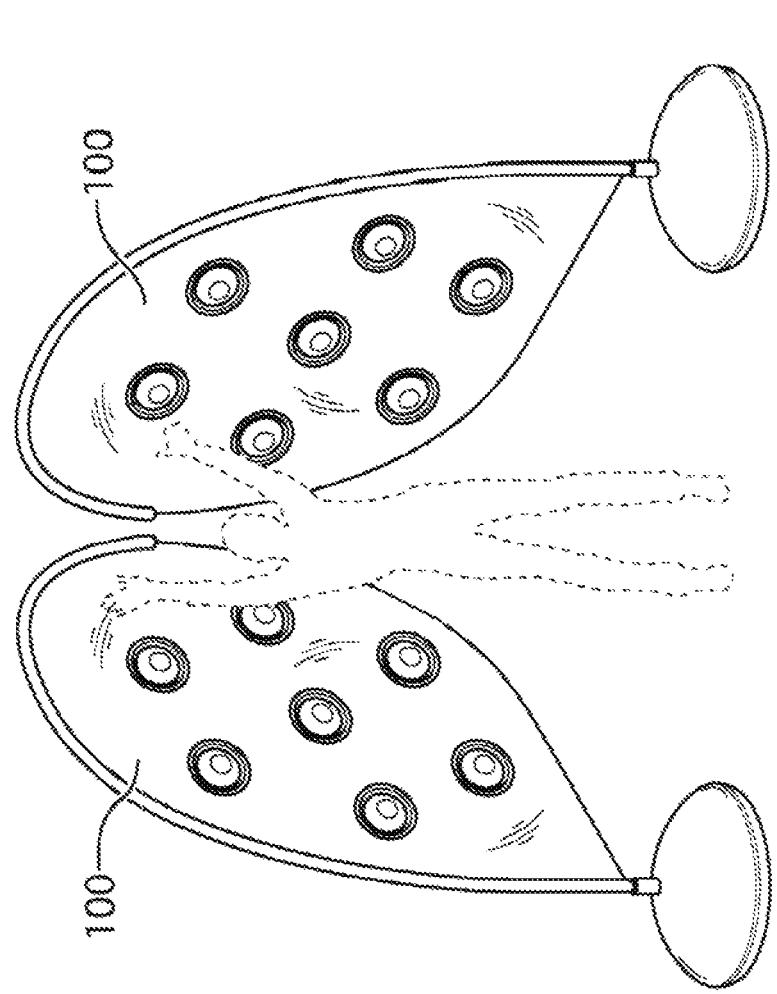
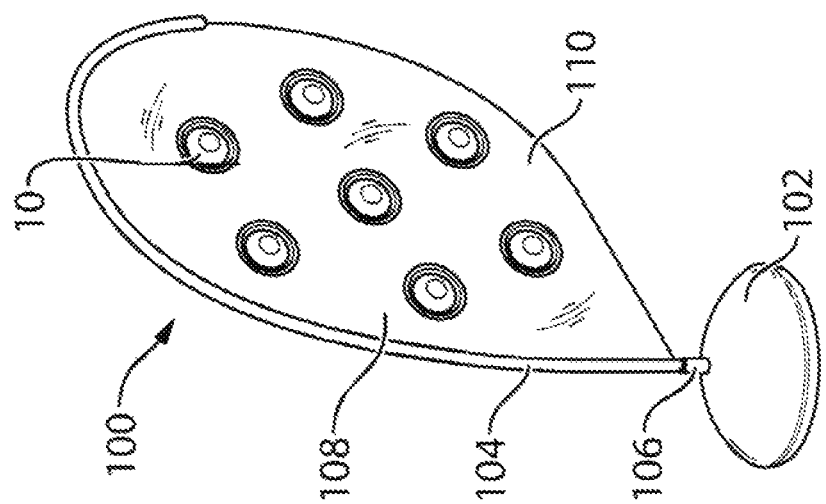

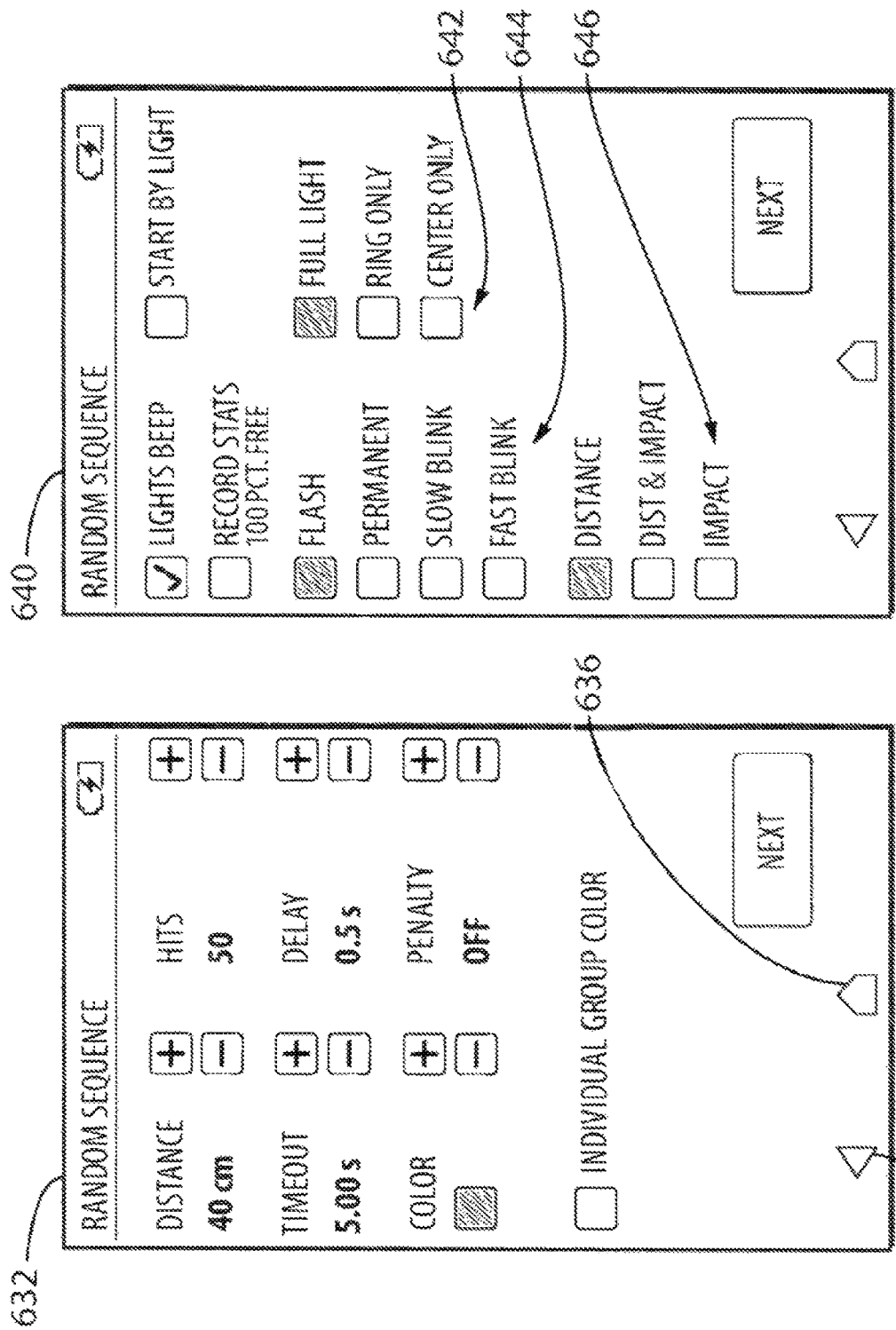

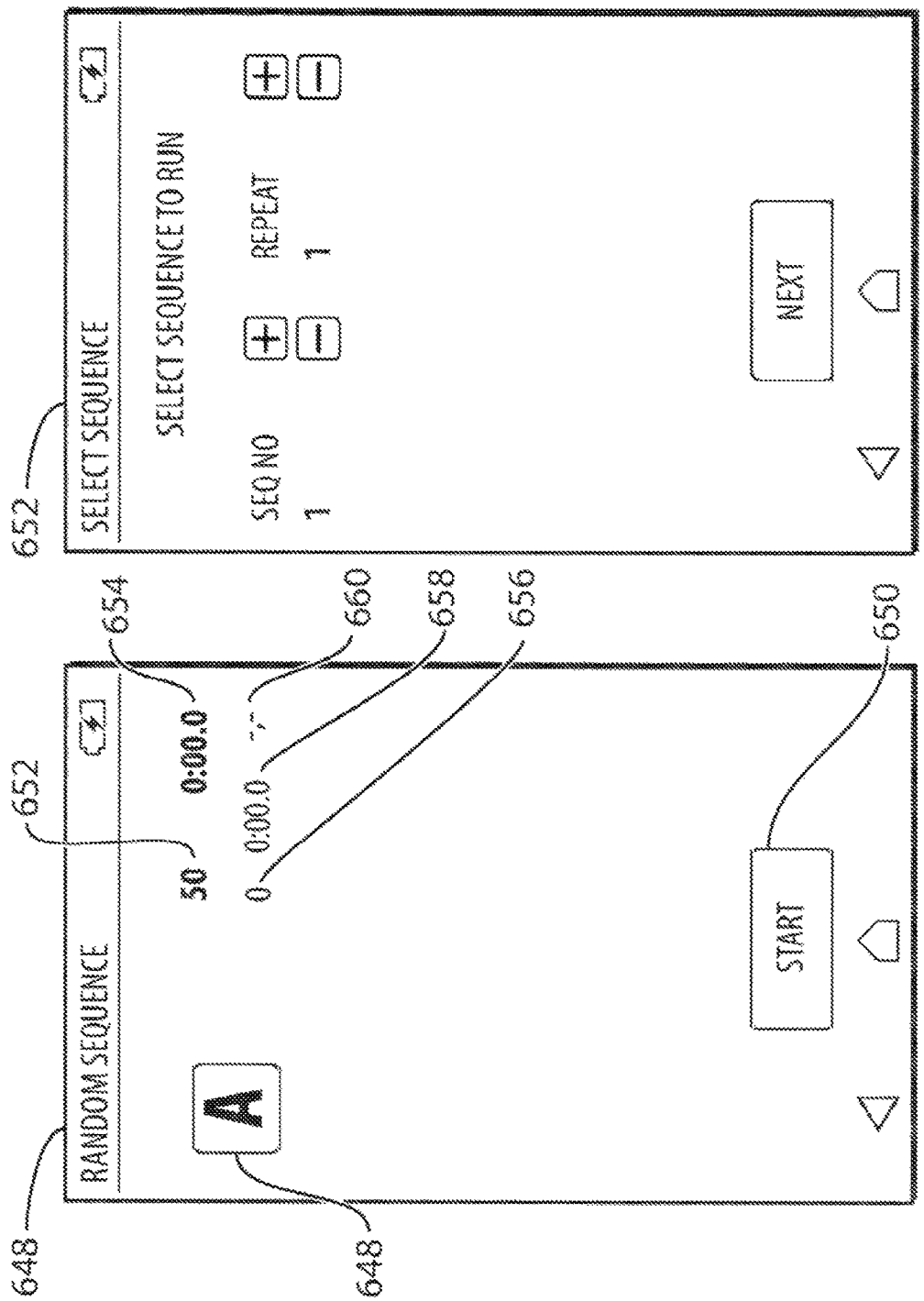

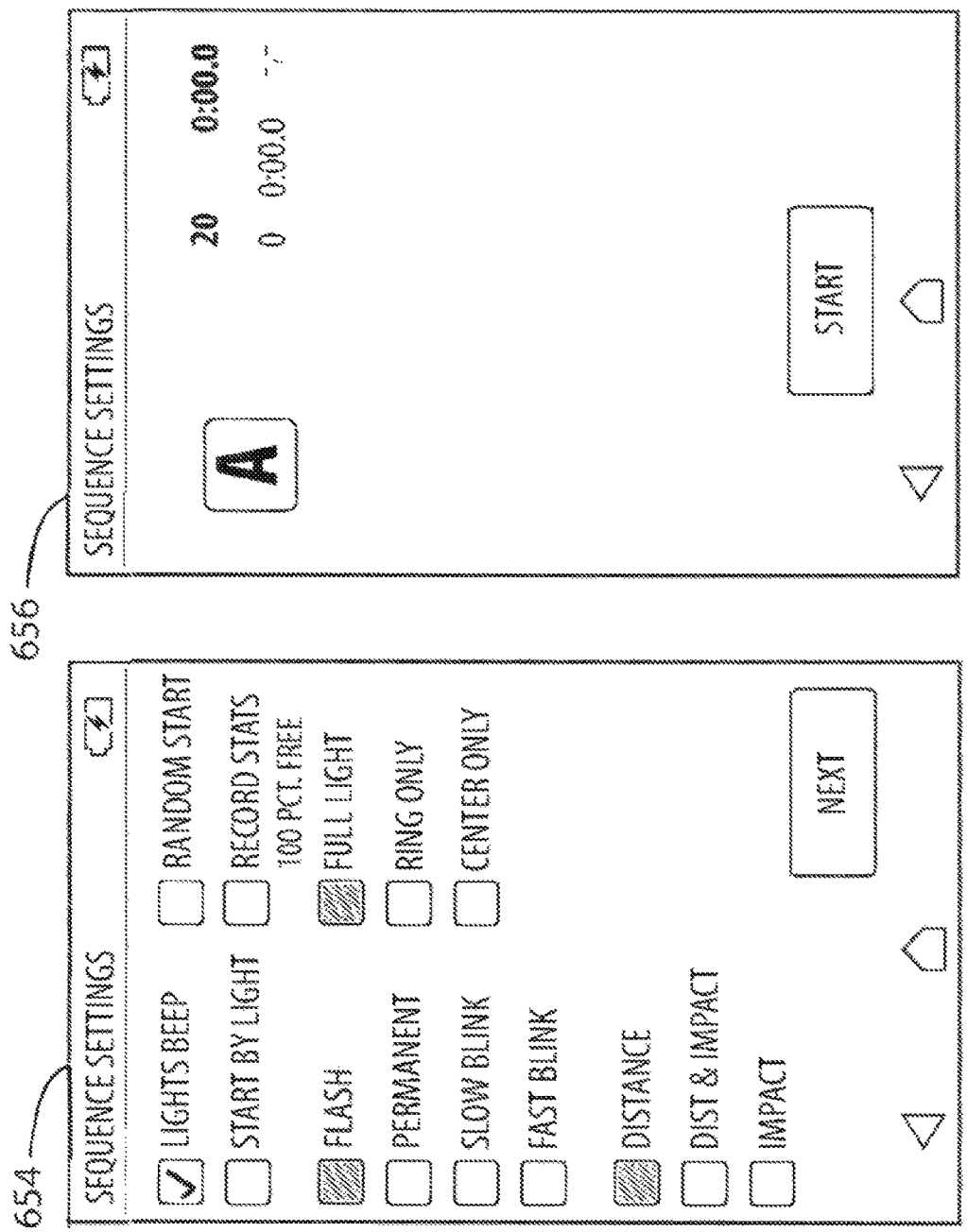

Fig. 31

CREATE SEQUENCES

▨ SETTING 1    ☐ SETTING 2

DISTANCE    ⊞ ⊟    TIMEOUT    ⊞ ⊟
40 cm              5.00 s

DELAY       ⊞ ⊟    COLOR      ⊞ ⊟
1.0 s              ▨

ON THE FOLLOWING SCREEN YOU WILL PAIR EACH FITLIGHT WITH ONE OF THE ABOVE SETTINGS.

[ NEXT ]

SELECT SEQUENCE

SELECT SEQUENCE TO RUN

SEQ NO    ⊞ ⊟    REPEAT    ⊞ ⊟
1              1

[ NEXT ]

▽    ◁

658

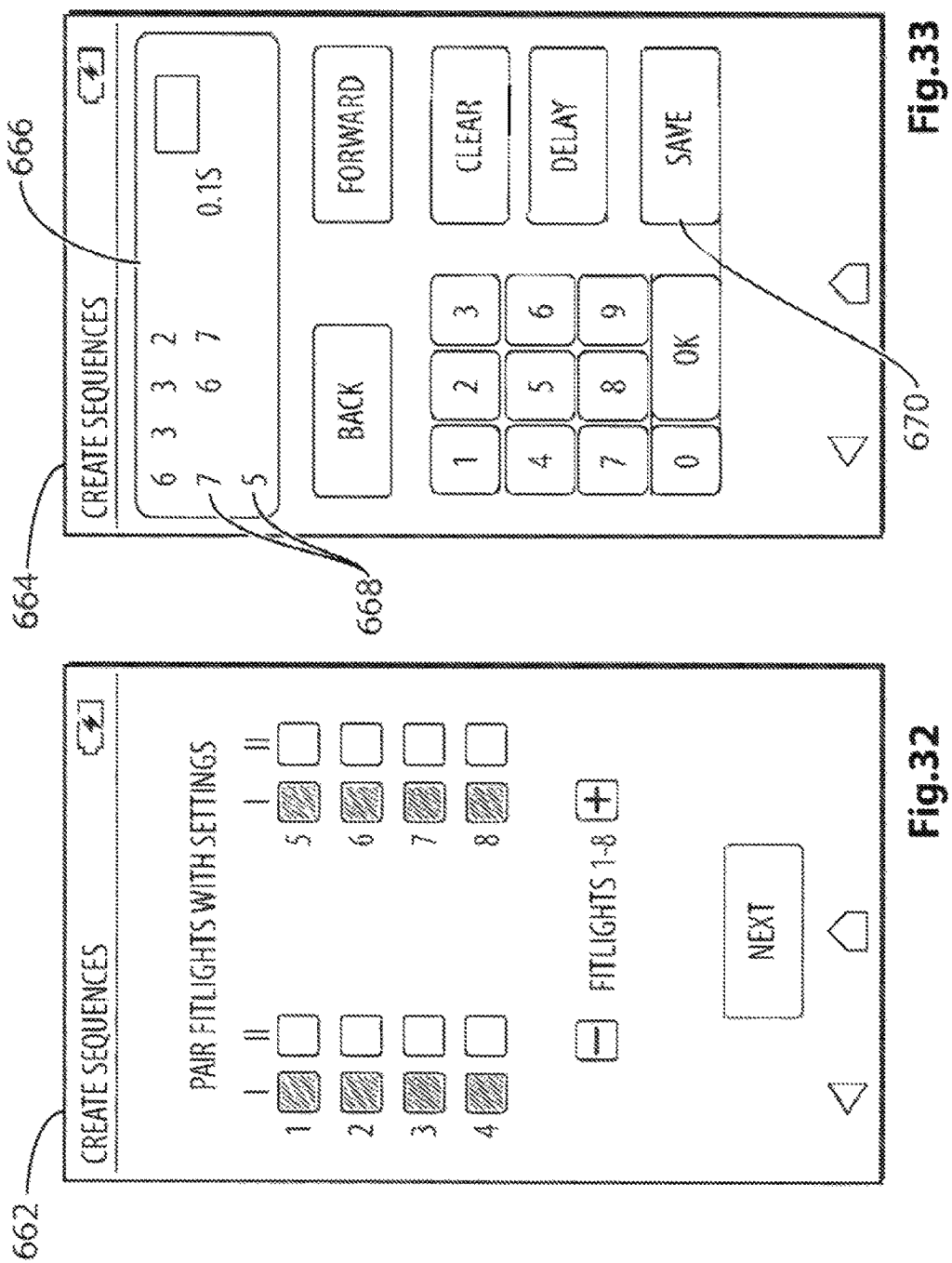

Fig. 35

SPLIT TIME TEST — 674

TAG ID
(NONE)

TIME  .:.-.

LIGHT NO   0.00

1  -:-.-
2  -:-.-
3  -:-.-
4  -:-.-
5  -:-.-
6  -:-.-
7  -:-.-
8  -:-.-

CLEAR   START 676, 675

Fig. 34

SPLIT TIME SETUP — 672

DISTANCE  [+] [−]
20 CM

COLOR  [+] [−]

[✓] START BY LIGHT
[✓] RECORD STATS
100 PCT. FREE

NEXT

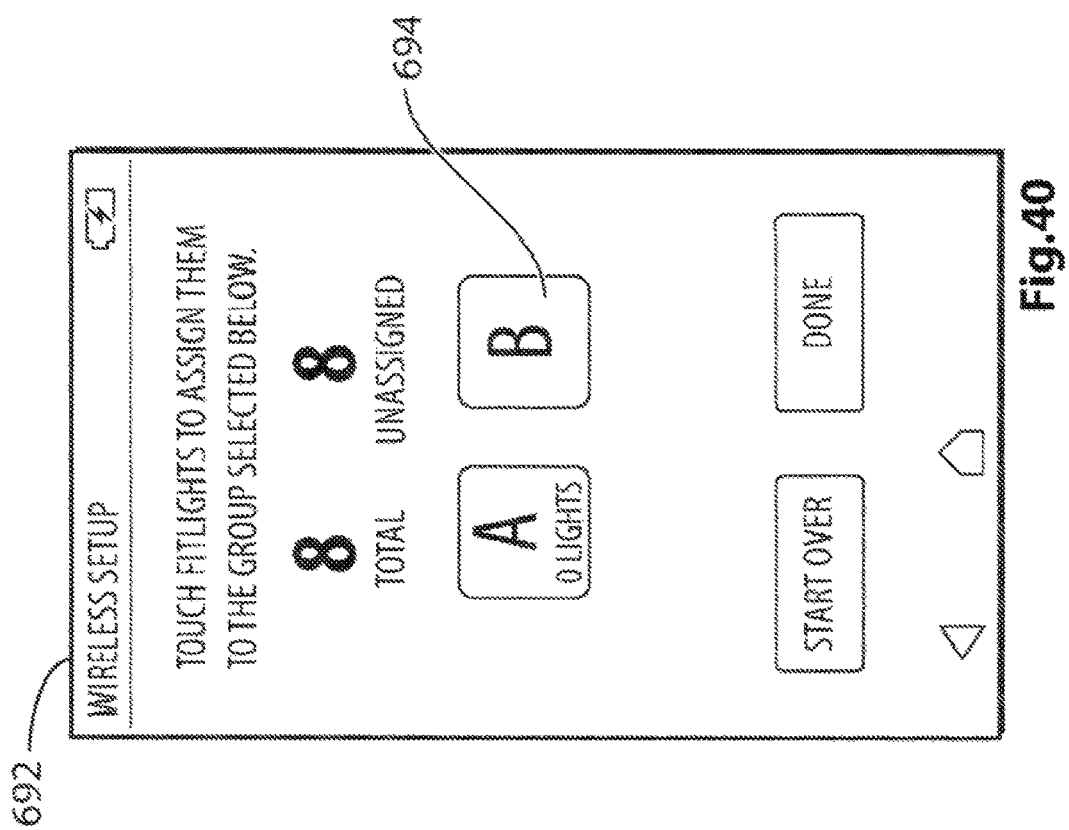

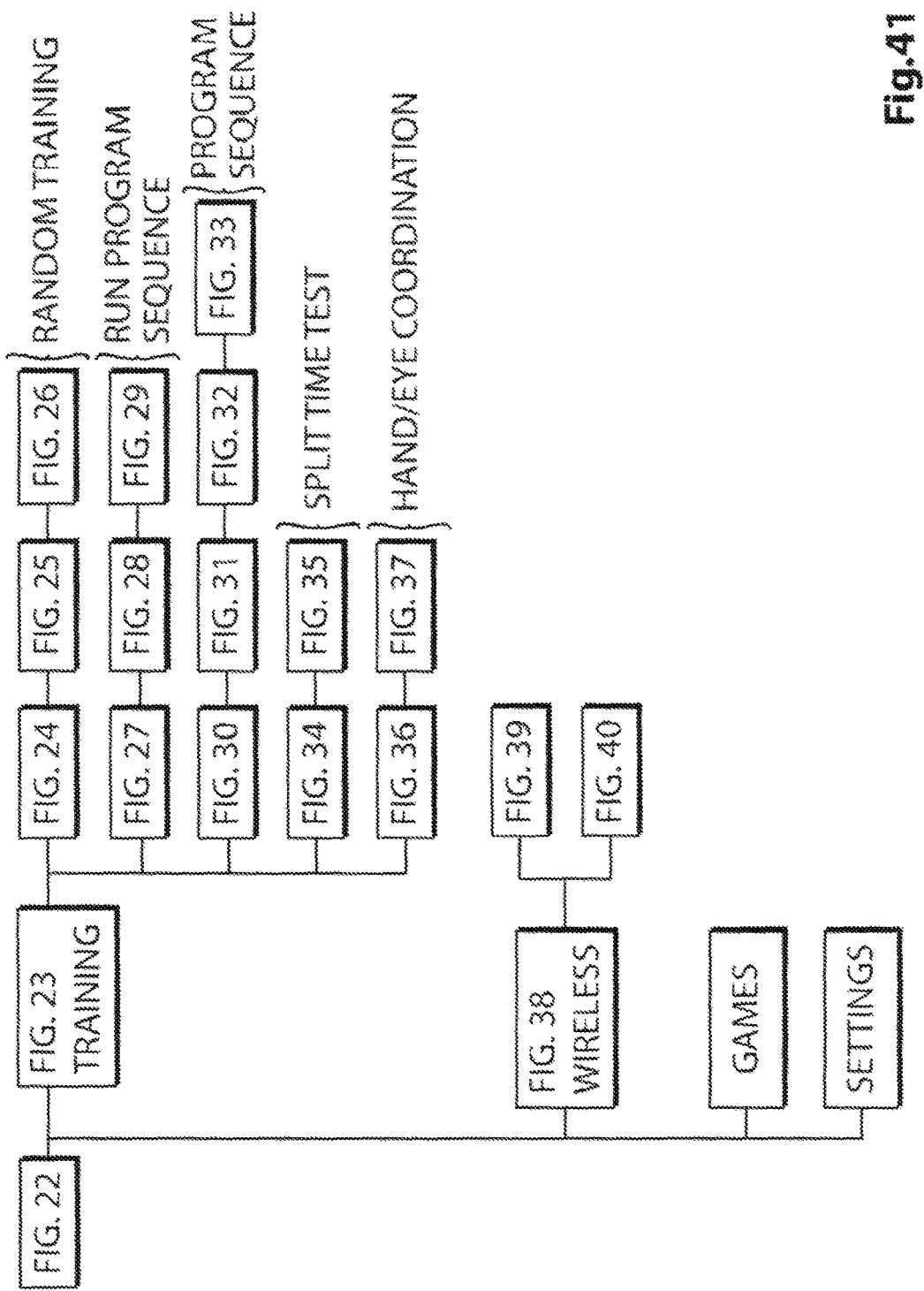

EXERCISE TRAINING SYSTEM

This application is a Continuation of U.S. patent application Ser. No. 14/356,448 which is a national phase entry application of PCT/CA2012/001048, filed Nov. 15, 2012, which claims the benefit of: U.S. Provisional Application No. 61/559,940, filed Nov. 15, 2011, the contents of all of which are incorporated herein by reference in their entireties.

FIELD

The invention relates generally to systems for exercising human reaction to stimuli and more particularly to apparatus for sports and rehabilitation exercises.

BACKGROUND

A variety of physical exercise apparatus which produce some form of stimulus to which a human being must respond are known in the art. The stimulus in such apparatus is typically a light source, and the person being trained must react to the light source, for example, by touching it, or moving into or out of the path of a light beam. Some systems have a number of such light sources which flash on and off in a predetermined sequence requiring the person being trained or exercising to react accordingly or to physically move to different locations. The reaction time between the onset of the light and the time it takes the person to react may also be measured as a performance metric.

An example of such a system is disclosed in EP 0 403 130 to Noble et al. entitled "Physical Exercise Apparatus" and published on Dec. 19, 1990. This system has a rack mounted on a wall on which a number of targets are mounted in vertical arrays. The targets have lights that are under the control of a computer which is programmed to flash the lights in a predetermined pattern. The system is intended for exercising racquet sports such as tennis or squash, and thus the person being exercised holds a wand or a stick which is used to hit a contact switch embedded in the target.

GB 2 270 004 to Nelson entitled "Physical Exercise Apparatus" and published on Mar. 2, 1994 discloses a similar system. This system is intended for training or exercising a boxer and also features a rack mounted on wall on which a number of targets are mounted in an orderly array. The targets have lights that are programmed to flash on and off in a predetermined pattern. The target members in this case have a force sensor in them (such as a piezo-electric element) to measure how hard the person strikes the target. The system also features a pressure mat or in the alternative a light beam for determining if the boxer steps outside a designated area.

US 2005/0167907 to Curkendall et al. entitled "Method and Apparatus for Portable Exercise System with Electronic Targets", published Aug. 4, 2005 discloses a portable racquet based exercise system with electronically-activated targets and a non-contact racquet. Each target contains a radio receiver that allows a controller transmitter to activate it. An active target alerts the player with a visual and/or auditory signal, directing the player to different areas of the virtual court. When a player's racquet is brought within the vicinity of the active target within an allotted time, the target designates a hit. The controller is embedded in the mobile racquet or wand and uses radio frequency signals to communicate with the targets, signalling which target to light up. The targets have infra-red (IR) emitters and the wand has an IR receiver in it so when the wand approaches the vicinity of a target and senses the IR signal, the controller registers a hit.

WO 2007/142588 to Rasmussen entitled "System for Exercising Human Reaction to Stimuli. Method and Computer Program Therefor and Use of the System", published Dec. 13, 2007 discloses a computer controlled system for generating stimuli such as a light and means for measuring a person's reactions to such stimuli.

SUMMARY

In many of the prior art systems, there is a need to either make physical contact with a target device or to move a device such as a wand to within a predetermined range of the target device. While this may be acceptable for some forms of sport training such as boxing or racquet sports, there are many instances where such hard limits are not conducive to training an individual. For example, in the field of rehabilitation, the range or reach of a person's movement can be an important criteria or metric in assessing the individual's performance. The invention therefore seeks to provide a more robust exercise system where the range or reach to successively register a hit to a target is a programmable parameter.

Accordingly, one aspect the invention provides a stimulant target unit which includes a housing; a stimulation source, such as a light source, mounted in the housing to stimulate a user; a proximity sensor mounted in the housing to provide an output of a distance between the unit and an external object; and feedback means for signaling the user that the unit has been actuated. A controller is connected to the stimulation source, the proximity sensor, and the feedback means. The controller signals the stimulation source to generate the stimulus, registers the user reaction to the stimulus by bringing a body part or other object to within a selected distance of the proximity sensor, and thereafter activates the feedback means to inform the user that the unit has been actuated. The selected proximity distance required to actuate the unit is user programmable.

In another aspect, the invention provides an exercise training system which includes a system controller and a plurality of stimulant target units connected via a wireless network to the system controller. Each stimulant target unit includes a light source providing light to stimulate a user, a proximity sensor providing an output of a distance between the proximity sensor and an object external to the unit, and feedback means for informing the user that the unit has been actuated. The system controller includes a program for activating the stimulant target units in a sequence. In executing the program, the system controller signals a given stimulant target unit to illuminate its light source. The given stimulant target unit registers an actuation thereof by the user in reaction to the illumination when the user brings a body part or other object to within a selected distance of the corresponding proximity sensor, and the given stimulant target thereafter activates its feedback means to inform the user that the given stimulant unit has been actuated. The selected proximity distance required to actuate the given stimulant target unit is programmable by the user.

The invention also seeks to provide a training system where the sequence of stimulant target units is easily programmable by the user. According to this aspect of the invention, the system controller is programmable via a learning mode in which the user actuates various stimulants target units in a sequence that is recorded by the system controller for subsequent playback. In addition, the user may select the proximity distance required to actuate the given stimulant target unit by bringing a body part or other object to the vicinity of the given stimulant target unit, where the closest distance is recorded as the selected actuation distance.

In the preferred embodiment, the number of stimulant target units constituting the system is dynamically configurable and discoverable upon power up of the system controller. To provide this functionality, the wireless network preferably operates in accordance with the ZigBee communication protocol.

The feedback means may be provided by one or more techniques or devices. These includes powering down the light source; causing the light source to display a different colour; causing the light source to display a predetermined sequence of flashes; illuminating a second light source; and generating an audio signal.

The proximity sensor may be provided by an infra-red distance sensor. Alternatively, the proximity sensor may be provided by an infra-red distance sensor in combination with at least one of an additional type of distance sensor. The additional sensor may include a capacitive proximity sensor or an ultrasonic proximity sensor. The distance provided by the proximity sensor may be an amalgamation of distance readings provided the infra-red distance sensor and the at least one additional type of distance sensor.

If desired, each stimulant target unit may also include an accelerometer for measuring force of physical contact with the unit, whereby the actuation of the stimulant target unit is registered in response to an output of the accelerometer.

In the preferred embodiment, the stimulant target member includes a lock member for attaching the unit to a support mounting accessory, such as a buckle which may attached to a support member via a strap. Alternatively, the lock member may be one part of a hook and loop fastener where the support mounting accessory provides the other part of the hook and loop fastener. In this case, the support mounting accessory may be a flag having the other part of the hook and loop fastener, wherein multiple stimulant target units are mounted on the flag.

More generally, and as described in greater detail below, the invention provides a wireless exercise or training system comprising multiple light stimulant target units and a central system controller. The system controller executes a training routine which activates the lights of the stimulant target units according to a programmed sequence. The athlete or individual being trained or rehabilitated (the user) reacts by actuating the lighted stimulant target units. Various measurements can be captured for immediate feedback in relation to the user's performance or can later be downloaded to a personal computer for future analysis. The stimulant target units can be actuated by use of the user's hands, feet, head, or by racquets or by any other sport specific means. The stimulant target units can be programmed to be actuated by full contact or proximity sensing whereby the system is able to record time for any athletic training function. The system is extremely easy to set up and use, and training routines can be pre-programmed into the controller or easily developed on site at a training facility.

In another aspect, a stimulant target unit is provided which includes: a housing; a stimulation source mounted in the housing for stimulating a user to actuate the unit; an infra-red sensor for detecting when a user has actuated the unit; and feedback means for informing the user that the unit has been successfully actuated. The housing has a translucent portion through which infra-red light is transmitted as the infra-red sensor operates. The translucent portion through which the infra-red light is transmitted is positioned at a highest elevation of the housing and configured to allow water to flow away from the infra-red sensor.

The translucent portion is preferably domed shaped.

In another aspect, a stimulant target unit is provided which includes: a housing; a stimulation source mounted in the housing for stimulating a user to actuate the unit; an actuation sensor mounted in the housing for detecting when a user has actuated the unit; and feedback means mounted in the housing for informing the user that the unit has been successfully actuated. The housing is characterized by having a first shell connected to a second shell via an elastomeric rim.

More particularly, the rim may have opposing first and second grooves. The first shell may have a first axially extending flange along a periphery thereof. The second shell may have a second axially extending flange along a periphery thereof. The first flange may be disposed in the first groove and the second flange may be disposed in the second groove. The first flange ordinarily does not bottom out in the first groove and the second flange ordinarily does not bottom out in the second groove thereby enabling the first shell to move axially relative to the second shell upon impact.

In another aspect, a stimulant target unit is provided which includes: a housing; a stimulation source mounted in the housing for stimulating a user to actuate the unit; an infra-red sensor for detecting when a user has actuated the unit, the infra-red sensor including at least one IR receiver and at least one IR emitter; and feedback means for informing the user that the unit has been successfully actuated. The housing has a translucent portion through which infra-red light is transmitted when the infra-red sensor operates. The housing includes a cover inboard the translucent portion. The cover is configured to include a first tube having an aperture pointing in the direction of the translucent portion and a second tube encompassing the first tube, the at least one IR receiver being disposed within the first tube and the at least one IR transmitter being disposed within the second tube.

The translucent portion is preferably a dome. The first tube is preferably centrally located within the housing to coincide with the highest elevation provided by the dome, and the second tube is preferably concentrically arranged about the first tube.

In another aspect, a stimulant target unit is provided which includes: a housing; a stimulation source mounted in the housing for stimulating a user to actuate the unit; an infra-red sensor for detecting when a user has actuated the unit, the infra-red sensor including at least one IR receiver and at least one IR emitter; and feedback means for informing the user that the unit has been successfully actuated. The infra-red sensor is operated to (i) detect a first condition where the at least one IR receiver conducts a first reading of IR light level above a first threshold irrespective of whether or not the at least one IR emitters are activated or deactivated, (ii) when the first condition is present, detect a second condition where the at least one IR receiver conducts a second reading of IR light level that is reduced in comparison to the first reading when the at least one IR emitter is active, and (iii) when the second condition is present, thereafter deactivating the at least one IR emitter and the at least one IT receiver conducts a third reading of IR light, whereupon in the event the third reading is below a second threshold the sensor determines that an object is proximate to the unit.

In another aspect, a stimulant target unit is provided which includes: a housing; a stimulation source mounted in the housing for stimulating a user to actuate the unit; an infra-red sensor for detecting when a user has actuated the unit, the infra-red sensor including at least one IR receiver and at least one IR emitter; and feedback means for informing the user that the unit has been successfully actuated. The infra-red sensor is operated to repeatedly cycle the at least one IR emitter on and off and the infra-red sensor determines that an object is proximate by detecting IR light level above a threshold for a plurality of consecutive cycles when the at least one IR emitter is on.

In another aspect, a stimulant target unit is provided which includes: a housing; a light source mounted in the housing, the light source providing light to stimulate a user; a proximity sensor mounted in the housing, the proximity sensor providing an output of distance between the proximity sensor and an object external of the housing; and feedback means for informing the user that the unit has been actuated. A controller is connected to the light source, the proximity sensor, and the feedback means, wherein the controller (i) signals the light source to illuminate, (ii) registers user reaction to the illumination in bringing a body part or other object to within a selected distance of the proximity sensor, and (iii) thereafter activates the feedback means to alert the user that the unit has been actuated. In the event the proximity sensor senses the body part or other object receding from the unit prior to the stimulation provided by the light source, the controller signals a false start event.

In another aspect, an exercise training system is provided which includes: a system controller; a plurality of stimulant target units (STUs) connected via a wireless network to the system controller, each STU including a light source providing light to stimulate a user, at least one of a proximity sensor and a contact sensor for registering an actuation of the STU by the user in response to the light stimulation, and feedback means for informing the user that the STU has been actuated. The user can program the system controller to activate the STUs in a user specified sequence. The user specifications include: (i) a time delay, being the time between the actuation of a STU in the sequence and the stimulation of a successively following STU in the sequence, and (ii) a timeout period, being a maximum period of time the system controller will wait to register an actuation of a STU in the sequence before stimulating a successively following STU in the sequence.

In another aspect, a stimulant target unit is provided which includes: a housing; first and second light sources mounted in the housing; a proximity sensor, mounted in the housing, for detecting proximity of an external object; a contact sensor, mounted in the housing, for detecting an external contact with the unit; feedback means for inform the user that the unit has been actuated; and a controller for programming the unit to stimulate the user by (i) activating the first light source, (ii) activating the second light source, or (iii) activating the first and the second light sources; and for programming the unit to register an actuation of the unit by (i) triggering the proximity sensor only, (ii) triggering the contact sensor only, and (ii) triggering the proximity sensor and the contact sensor.

BRIEF DESCRIPTION OF DRAWINGS

The foregoing and other aspects of the invention will be more readily appreciated having regard to the attached drawings, wherein:

FIGS. 8A, 8B and 8C are perspective views of a flag stand (or stands) for mounting one or more stimulant target units;

FIG. 24 shows a first input screen displaying icons associated with a Random training function;

FIG. 25 shows a second input display screen displaying icons associated with the Random training function;

FIG. 26 shows a performance display screen relating to the Random training function;

FIG. 27 shows a first input screen displaying icons associated with a Programmed Sequence training function;

FIG. 28 shows a second input screen displaying icons associated with the Programmed Sequence training function;

FIG. 29 shows a performance display screen relating to the Programmed Sequence training function;

FIG. 30 shows another first input screen displaying icons associated with a Programmed Sequence training function;

FIG. 31 shows a second input screen displaying icons representing inputs related to the Programmed Sequence training function;

FIG. 32 shows a third input screen displaying icons representing further inputs related to the Programmed Sequence training function;

FIG. 33 shows a fourth input screen displaying icons representing further inputs related to the Programmed Sequence training function;

FIG. 34 shows an input screen displaying icons relating to a Split time function;

FIG. 35 shows a performance display screen relating to the Split time function;

FIG. 36 shows an input screen displaying icons relating to a Hand/Eye coordination function;

FIG. 37 shows a performance display screen relating to the Hand/Eye coordination function;

FIG. 40 shows a second input screen relating to the Wireless function that is displayed when a second check box is checked on the screen shown in FIG. 38; and FIG. 41 is a schematic diagram illustrating the display order of the display screens shown in FIGS. 22-40.

DETAILED DESCRIPTION OF PREFERRED EMBODIMENTS

Figure 1:
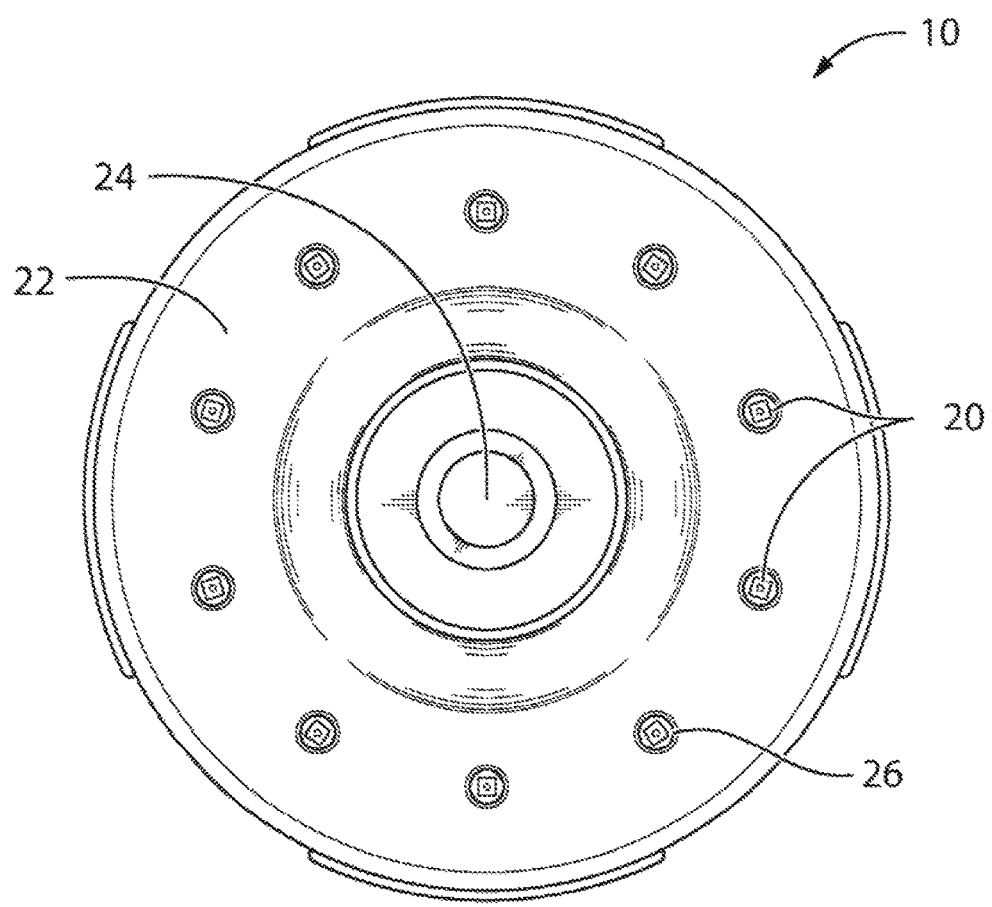
FIG. 1 is a top perspective view of a stimulant target unit according to a first preferred embodiment of the invention.

FIG. 1 shows a perspective view of a stimulant target unit 10. As discussed in greater detail below an exercise training system according to a preferred embodiment of the invention utilizes a network of the stimulant target units 10. The stimulant target unit 10 preferably provides stimulation to the person exercising (i.e., the user) in the form of light and provides feedback to the user that is preferably also in the form of light.

Figure 2:
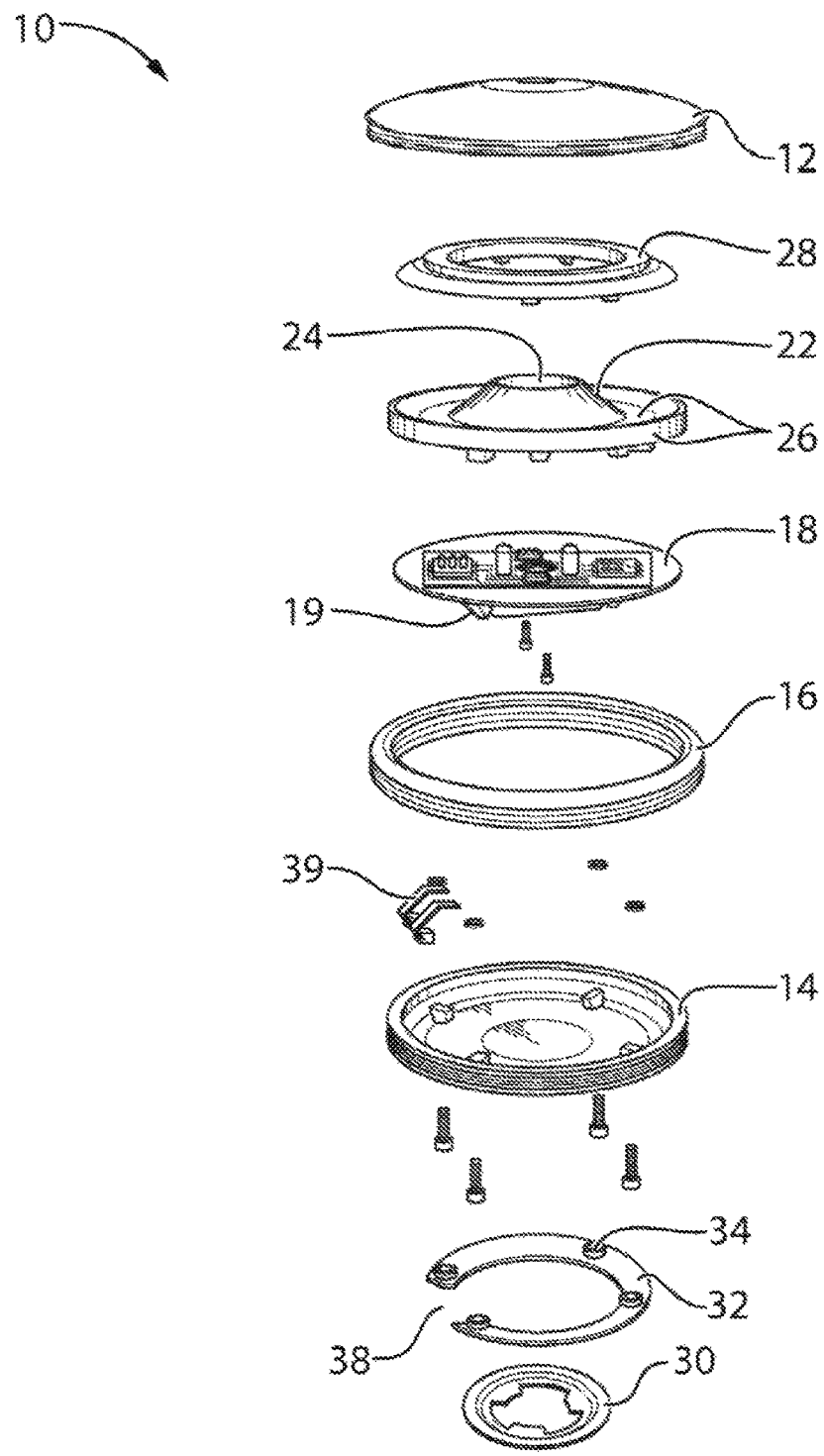
FIG. 2 is an exploded view of the stimulant target unit shown in FIG. 1.

FIG. 2 shows an exploded view of the stimulant target unit 10. The unit 10 includes a translucent upper shell 12 and an opaque lower shell 14 which together form the majority of a housing. A rim 16 surrounds the upper and lower shells 12, 14 to join the two parts along their peripheries or, where the shells are directly connectable to each other, to hide the seam therebetween.

A printed circuit board (PCB) 18 is mounted to the bottom shell 14. The underside of the PCB 18 preferably has a battery compartment 19 mounted thereon with rechargeable batteries. The PCB 18 carries essential circuit components for generating originating stimulus, measuring reaction or response time of the individual being exercised or trained, and generating feedback stimulus for the trainee to confirm that he or she has adequately responded to the stimulus.

More particularly, as seen best in FIG. 1 the printed circuit board 18 has an annular arrangement of light emitting diodes (LEDs) 20. An inner cover 22 sits over the PCB 18. The inner cover 22 has a large central aperture 24 and a series of small holes 26 annularly arranged to coincide with the position of the LEDs 20 so that the light from these devices shine through the inner cover 22. If desired, an annular light guide, diffuser or light pipe 28 may be mounted over the inner cover 22 to spread the light generated by the LEDs 20 and provide a more uniform light in the shape of a ring as opposed to a series of point sources.

The central aperture 26 provides a window to response measuring sensors such as infra-red, ultrasonic or capacitive sensors mounted on the PCB 18. The response measuring sensor(s) register a successful actuation or "hit" of the stimulant target unit 10 as discussed in greater detail below.

The annular array of LEDS 20 preferably provide originating stimulus by being turned on, and preferably also provide feedback stimulus by being turned off. If desired, the LEDS 20 can be red-green-blue light emitting diodes in which case the LEDs 20 can provide feedback stimulus by flashing a different colour of light, or by flashing a different sequence such as two quick on and off bursts. In addition or in the alternative, the PCB may also carry feedback stimulus such as LEDs that flash (either the same colour or a different colour) through the central aperture 26. Additionally or alternatively, feedback stimulus may be provided through a speaker (not shown) connected to the PCB 18.

Figure 3:
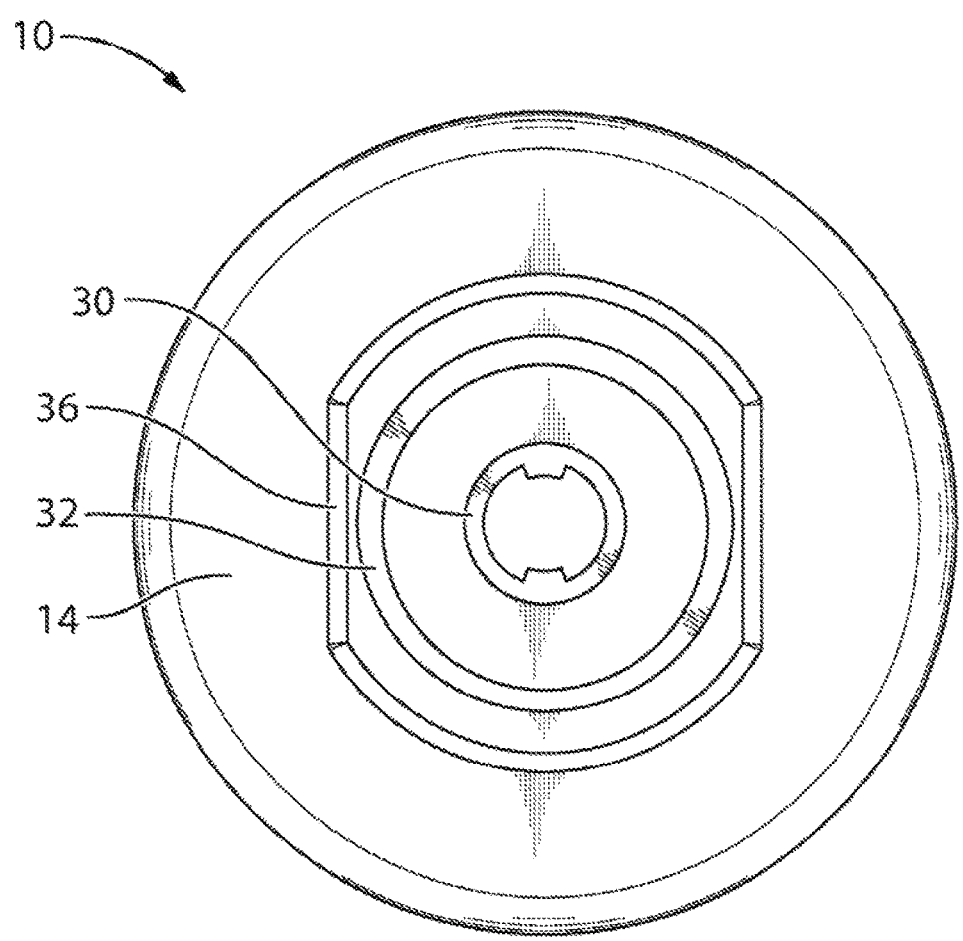
FIG. 3 is a bottom perspective view of the stimulant target unit shown in FIG. 1.

Referring additionally to the bottom view of the stimulant target unit 10 in FIG. 3, a base is preferably attached the bottom shell 14. In the illustrated embodiment the base is preferably provided by a lock member 30 which is held to the bottom shell 14 by a locking rim 32 that is preferably removably secured to the bottom shell 14, for example, by utilizing lugs 34 that inter-engage with corresponding features or rebates on the underside of the bottom shell 14. The removable locking rim 32 allows the lock member 30, which is used to secure the stimulant target unit 10 to a support structure, to be interchanged with a different lock member depending on the fastening requirements. In addition, a rubberized or foam profile 36 (seen in FIG. 3) may be bonded to the bottom shell 14 to function as a compression member if the stimulant target unit 10 is attached to a support structure via the lock member 30 or merely as an anti-slip ring if the stimulant target unit 10 is merely placed on a surface.

Figure 4:
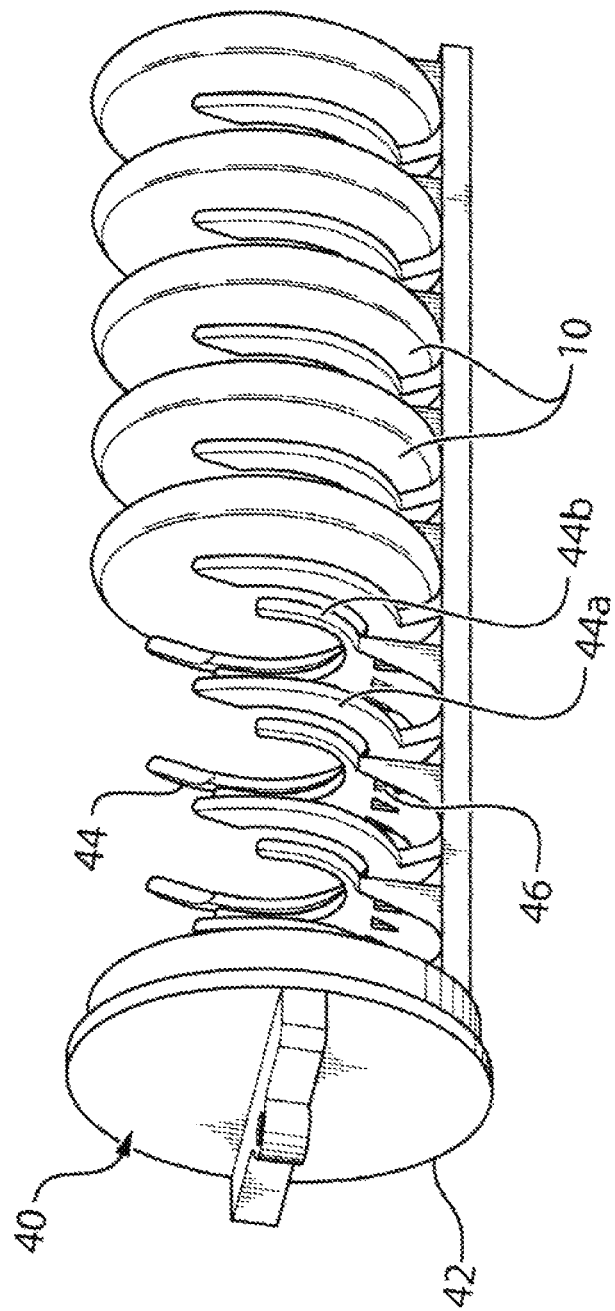
FIG. 4 is a perspective view of a battery charging assembly for charging multiple stimulant target units of the type shown in FIG. 1.

Referring particularly to FIG. 3, compartment 19 preferably have a metallized external charging ports 39 accessible through the bottom shell 14 (aperture not shown) which can be used to recharge the batteries in the compartment 19 without having to remove them. For this purpose, the locking ring 32 is semicircular in form, having an open sector 38. Preferably, as seen in FIG. 4, multiple stimulant target units 10 can be recharged at once in a recharging unit 40. The recharging unit 40 features a rack 42 with U-shaped stands 44 for holding multiple stimulant target units 10. Each U-shaped stand 44 has front and rear semicircular walls 44a, 44b for holding the stimulant target unit 10, with the base or bight of the U-shaped stand 44 having charging prongs 46 that contact the charging ports on the battery compartment 18 through the open sector 38 of the locking ring 32. The rack 42 may be mounted in a cylindrical housing (not shown) for securing the entire package.

Figure 5:
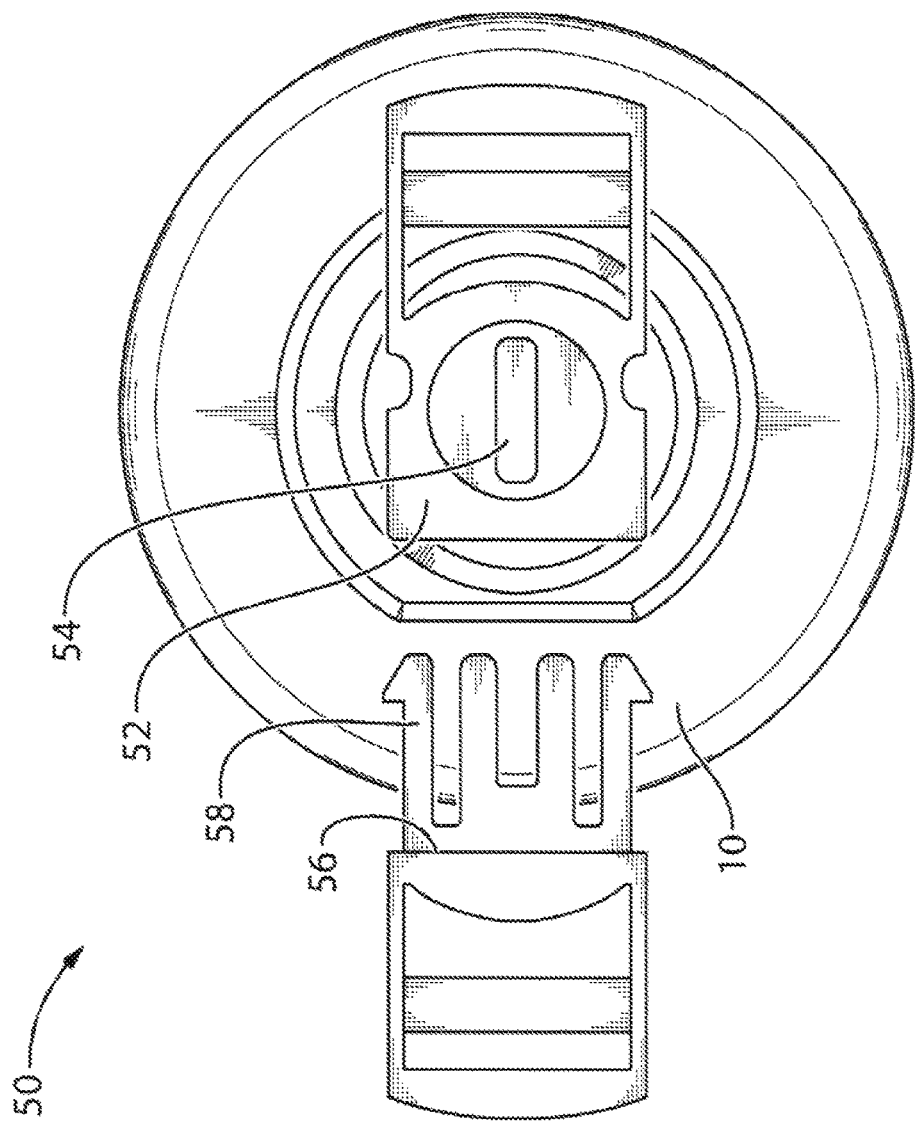
FIG. 5 is a perspective view of a mounting accessory for the stimulant target unit shown in FIG. 1.

FIG. 5 shows a buckle mounting accessory 50 which may be used to attach the stimulant target unit 10 to a support. The buckle mounting accessory 50 features a female part 52 that interconnects via a knob 54 with the lock member 30 of the stimulant target unit bottom shell 14. A male part 56 of the buckle mounting accessory 50 has flexible prongs 58 for insertion into the female part 52 and a flexible belt (not shown) wound around a support ties the male and female parts 52, 56 together. The buckle mounting accessory 50 provides a nearly universal mounting means.

Figure 6:
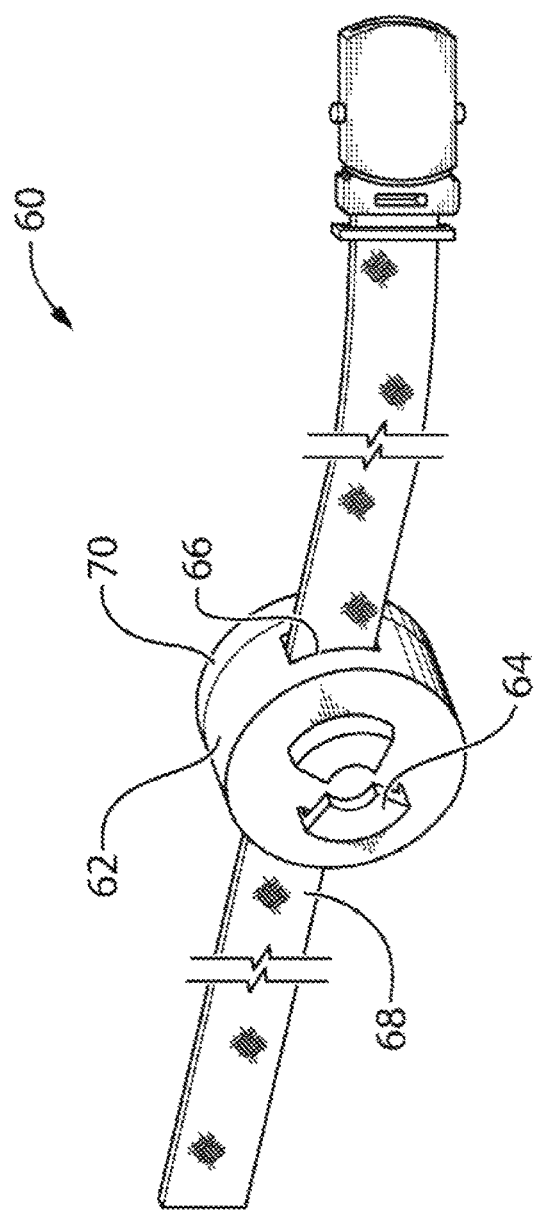
FIG. 6 is a perspective view of an alternative mounting accessory for the stimulant target unit shown in FIG. 1.

FIG. 6 shows another mounting accessory 60 which has a cylindrical body 62 in which an end face thereof has a lock member 64 complementary to the lock member 30 of the stimulant target unit bottom shell 14. The cylindrical body 62 has a through-hole 66 for a belt or strap 68 with buckle which may be used to fasten the mounting accessory 60 to a support. The opposing end face of the cylindrical body 62 has an anti-slide rubber surface 70 for gripping the support.

Figure 7:
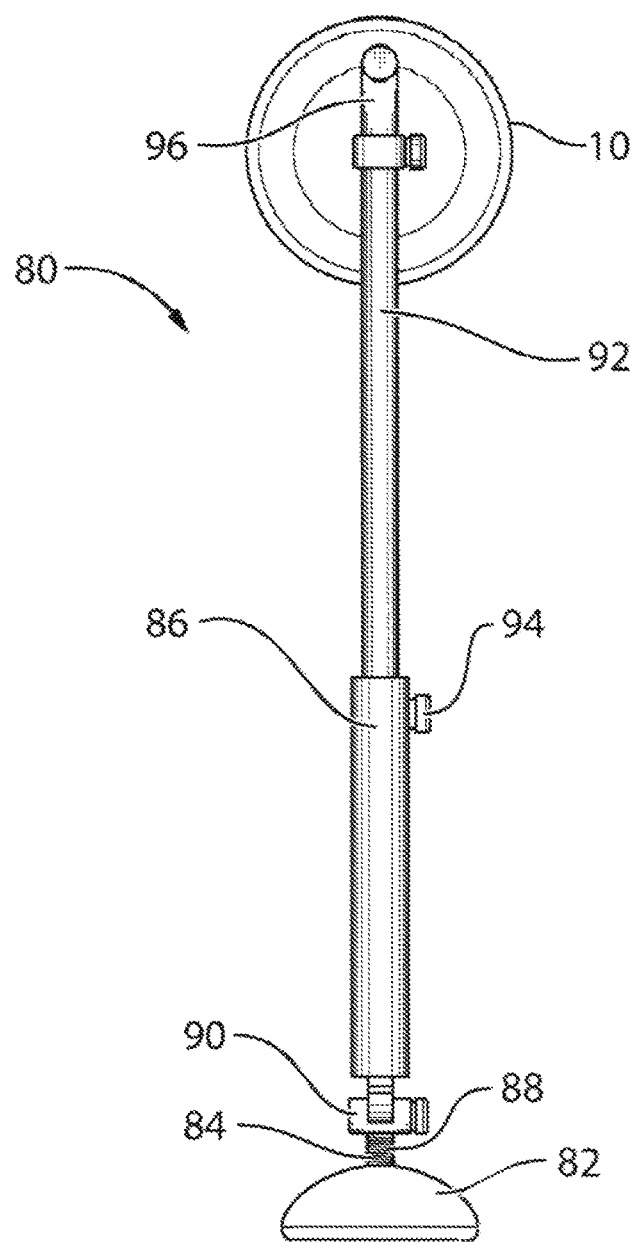
FIG. 7 is a perspective view of a stand for mounting stimulant target units.

FIG. 7 shows a stand 80 which can be used to mount and position the stimulant target unit 10 at a variety of positions above the ground. The stand has a heavy base 82 with a stem 84 capable of rotating 360 degree swivel. A pole 86 is pivotally mounted to the stem and biased to remain upright by a tensioning spring 88. The pivot mount has a knob 90 for maintaining the angle of the pole relative to the ground. The pole 86 has a telescopic portion 92 whose length is controlled by a second knob 94. The telescopic portion 92 has at its other end a goose neck 96 on which the stimulant target unit 10 can be fastened with either mounting accessory 50 or 60. The stand 80 is particularly useful where the stimulant target units are utilized as a part of a system for exercising running manoeuvres, e.g., to train football players.

Figure 8C:
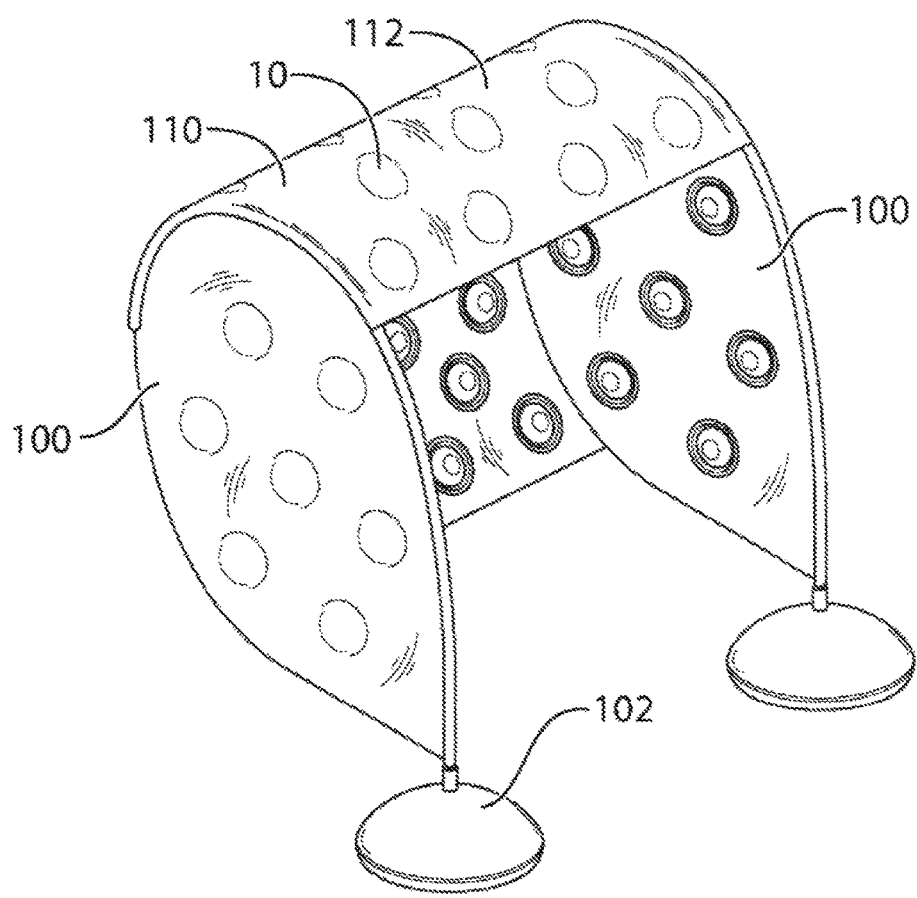

FIG. 8A shows a flag stand 100 which can be used to mount and position multiple stimulant target units 10 at a variety of positions. The flag stand 100 has a heavy base 102 into which a lightweight flexible pole 104 is mounted and tensioned to remain upright via a spring 106. The pole 104 is somewhat curved and functions as a spine for a cloth substrate 108. The cloth substrate 108 preferably features a hook surface 110 for a hook and loop fastener. The stimulant target units 10 preferably have a complementary lock member with a loop surface backing 112 which can be stuck anywhere on the cloth substrate 108. The flag stand 100 can be used individually to mount one or more stimulant target units 10 for a variety of purposes, or in pairs. For example, FIG. 8B shows two flag stands 100 disposed in mirror configuration. This configuration is particularly useful for handball or volleyball training. Likewise, FIG. 8C shows two flag stands 100 disposed in a parallel configuration with a hook and loop overhang 112 connecting the two stands 100 to provide a three-dimensional arrangement that would also be useful for training in sports such as handball or volleyball. As discussed below, the stimulant target units 10 can be set up so that it is not necessary to actually touch the unit in order to actuate it or register a "hit".

Figure 9:
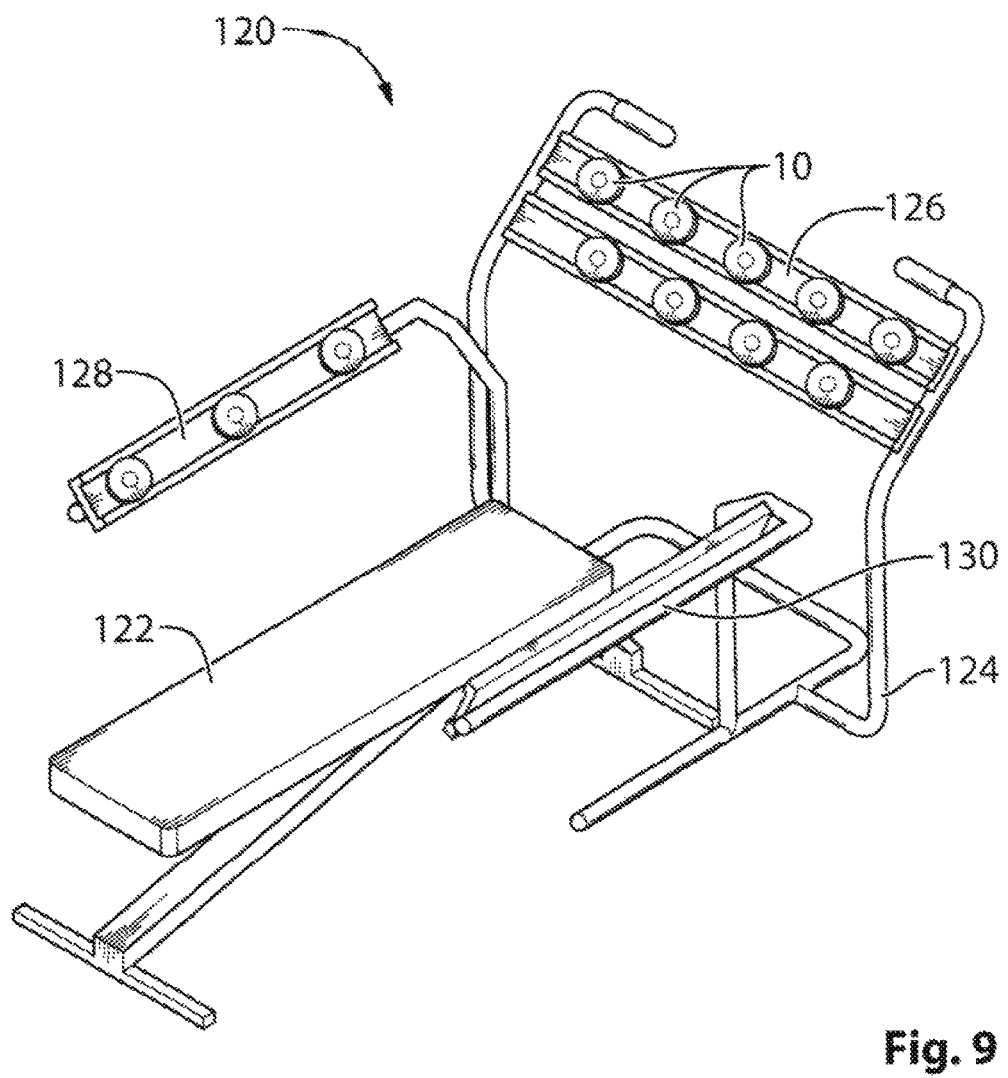
FIG. 9 is a perspective view of a weight training system that employs a number of the stimulant target units shown in FIG. 1, which surround a bench.

FIG. 9 shows a weight training system 120 in which the stimulant target units 10 surround a bench 122. The stimulant target units 10 are mounted on a frame 124 that has shelves 126, 128, and 130 located to the front, left and right of the bench, respectively. The angle of each shelf 126, 128, and 130 may be adjusted. This set-up is particularly useful for sit up exercises where the torso is directed toward stimulant target units 10 at different locations. The stimulant target units 10 are capable of measuring the torso position as it is not necessary to touch the units in order to actuate them or register a "hit". Rather, as described in greater detail below, the person's distance to the stimulant target units can be a programmable parameters that preferably functions as part of the training or exercising program. This feature is useful in that it can be used in particular for the rehabilitation of injuries whereby a progressive routine of various stretching exercises are required at different distances as the user recovers and the results are measured to gauge the patient's state of recovery.

Having discussed the physical characteristics of the preferred stimulant target units 10 and the manner in which they may be deployed in an exercise training system, the discussion will now expand upon the electronics utilized in the preferred stimulant target units 10.

Figure 10:
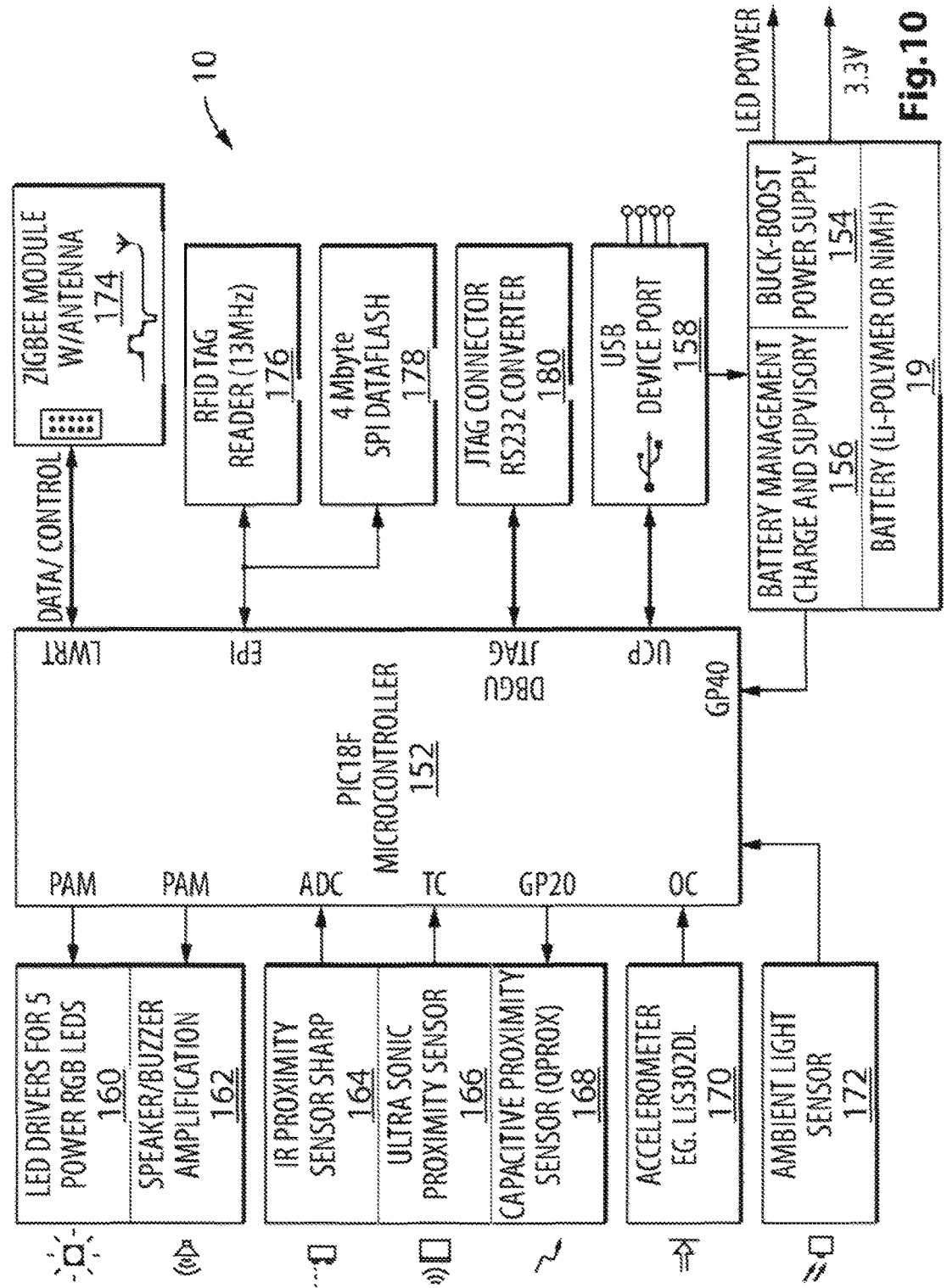
FIG. 10 is a system block diagram for the electronics employed in the stimulant target unit shown in FIG. 1.

FIG. 10 shows a system block diagram of the major electronic components used in stimulant target unit 10. The unit 10 includes a central microcontroller 152, such as a Microchip® PIC18F, which is powered by rechargeable batteries via a buck-boost power supply 154 that is supervised by a battery management circuit 156. A universal serial bus port (USB) 158 is connected to the microcontroller 152 and the battery management circuit 156. In addition, the microcontroller is connected to memory 178 and a JTAG connector 178.

The central microcontroller 152 controls the stimulus LEDS 26 via LED drivers 160 and an ambient light sensor 172, which is used to control the power supplied by LED drivers 160. More particularly, stimulant target unit 10 has the capability of generating different colors when red, green and blue (RGB) light emitting diodes 26 are employed. This allows software executed by the microcontroller to generate different colors of stimulating light. This capability allows the user to program exercise or rehabilitation routines where, for example, only red lights are deactivated and green ones are not. This allows the system to test user reaction and speed of recognition, or it allows the user to exercise their cognitive and memory skills by activating only certain color lights that may come on momentarily with various other colors.

The intensity of the light generated by the LEDs 26 is automatically adjustable by the microcontroller to accommodate various ambient light conditions. In particular, it is desirable to have very visible light in direct sunlight. Thus, the ambient light sensor provides feedback for adapting the intensity of the LEDs 26.

A speaker with amplification circuit 162 is also connected to the microcontroller 152 for providing audio feedback to users.

The micro-controller 152 is also connected to at least one of an infrared proximity sensor 164, an ultrasonic proximity sensor 166, and a capacitive proximity sensor 168. In addition, an accelerometer 170 or an optional contact switch 171 is provided for sensing physical contact with the user.

In the preferred embodiment the proximity sensor(s) senses the distance between a user's body part, such as a hand, and the stimulant target unit 10. A variety of commercially available components are capable of providing such a function. For example, Sharp manufactures a series of GP2XX™ IR proximity detectors, one of which (e.g., the GP2D120) may be suitable for this application. Similarly, Honeywell manufactures a line of UHZ™ series ultrasonic proximity sensors and Quantum Research Group manufactures a line of Qprox™ capacitive proximity sensors, one of which may be used in this application. In order to obtain the best estimate of distance the preferred embodiment employs different types of proximity sensors and utilizes the results from these devices to either ascertain the veracity of a primary reading device (e.g., the infrared sensor) or to average the readings from the different sensors to arrive at a conclusion. If desired, the microcontroller 152 may execute a Kalman filter to provide better confidence of the distance estimate readings obtained from the different types of proximity sensors.

The accelerometer 170 may also be used to register an actuation of the stimulant target unit. The actuation may be as simple as sensing a change in the accelerometer to indicate the presence of a physical contact. Alternatively, the actuation may require sensing a more complex signal corresponding to a given force at a certain direction as may be provided by a three axis accelerometer and suitable signal processing algorithms as known in the art per se. This feature would be useful if the stimulant target unit is embodied in a boxing or karate training program where the measurement of force as well as the angle of attack is a desired performance metric.

The microcontroller 152 is also preferably connected to a wireless personal area network (PAN) communication controller (with antenna) 174, and a radio frequency identification (RFID) tag reader 176, which may be provided by a commercial Zigbee or IEEE 802.15.4 personal area network integrated circuit (IC). The purpose of these components will become clearer in conjunction with an appreciation of the system controller.

Figure 11:
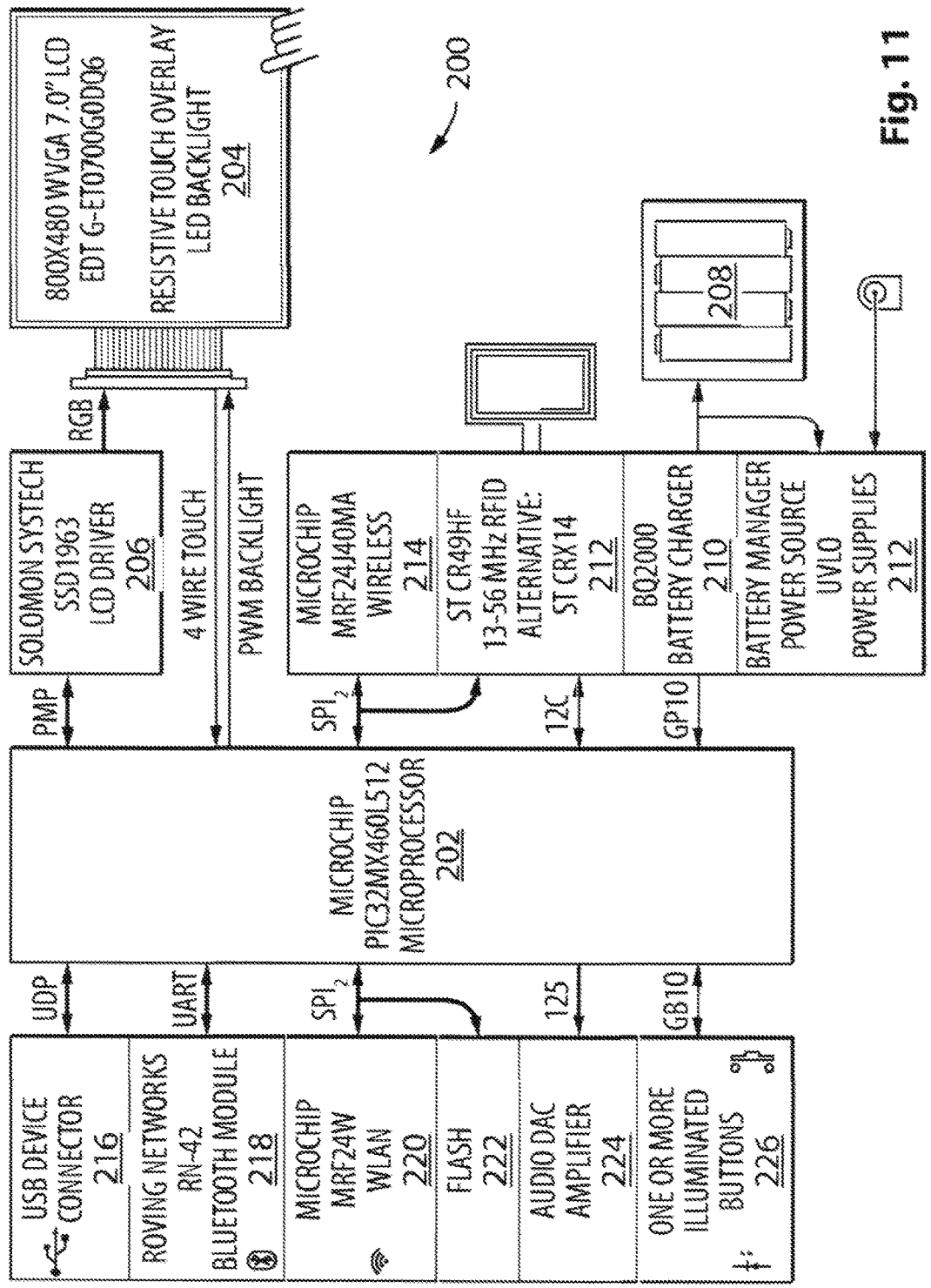
FIG. 11 is a system block diagram for the electronics employed in a system controller that manages multiple stimulant target units as part of a cohesive network.

FIG. 11 shows a system block diagram of a system controller 200. The system controller 200 has a central microprocessor 202, such as Microchip® PIC32MX460L512, which is connected to a touch sensitive liquid crystal display (LCD) screen 204 via an LCD driver 206. The system controller 200 is also powered by rechargeable batteries 208 via battery charge and management circuits 210 and 212. An RFID tag reader/writer 212 and a personal area network controller 214, such as a Microchip® MRF24J40MA Zigbee transceiver, are also connected to the microprocessor 202. Likewise, the microprocessor 202 is connected to a universal serial bus port 216; a Bluetooth circuit 218; a wireless LAN circuit 220; memory 222; an audio controller 224; and one or more illuminated push buttons 226.

Figure 12:
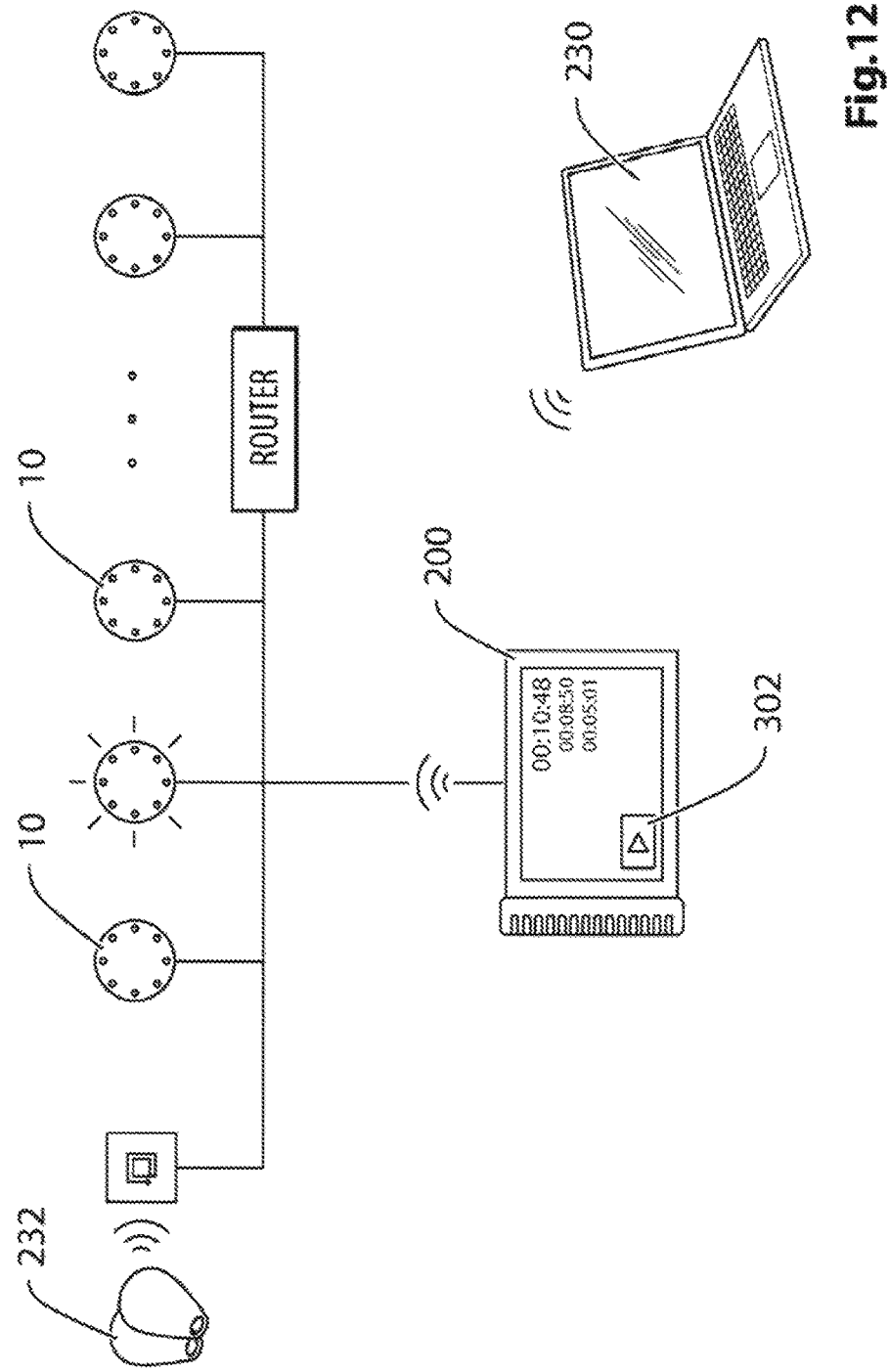
FIG. 12 is a schematic network diagram of an exercise or training system comprising the system controller shown in FIG. 11 with multiple stimulant target units shown in FIG. 10.

Referring additionally to the network diagram of FIG. 12, the system controller 200 preferably functions as the coordinator of a ZigBee (or similar) wireless network where the stimulant target units 10 function as ZigBee end devices. The system controller 200 initiates a wireless network and discovers the number of stimulant target units 10 within reception range. The system controller 200 also receives requests from recently turned on stimulant target units 10 to join the system managed by the system controller 200. This enables a user to rapidly and dynamically configure the number of stimulant target units 10 that compose the exercise or training system.

Once the wireless network is established, communication occurs wirelessly over RF channel(s). The system controller 200 maintains a set of instructions, that may be entered in or otherwise programmed by the user as described in greater detail below, that preferably sequences: (i) which stimulant target units 10 should light up (and if applicable or desired, the colour of light); (ii) the proximity distance to register a "hit" for the stimulant target unit in question; and (iii) the time delay to the activation of the next stimulant target unit 10 in the sequence. The proximity distance may be zero to force the user to physically touch the stimulant target unit in question in order to set off the impact measuring sensor, i.e., the accelerometer and/or contact switch. The time delay may also be zero, in which case two stimulant target units 10 will light up together. Thus, communicating over the wireless RF channel(s), the system controller 200 signals a specific stimulant target unit 10 to light up. In turn, when a specific stimulant target unit is actuated it wirelessly signals the system controller accordingly. The system controller 200 can measure the time delay between the stimulus and response, or, for more precision, each stimulant target unit 10 can measure the user response time and transmit it to the system controller 200 for recordal.

The system controller 200 may be programmed through conventional keyboard input via touch screen or keypad input. Or, as indicated in FIG. 12, the system controller 200 can interface with a personal computer or laptop 230 via the wireless LAN 220 or universal serial bus 216. The laptop 230 can execute a more elaborate user interface program.

Figure 13:
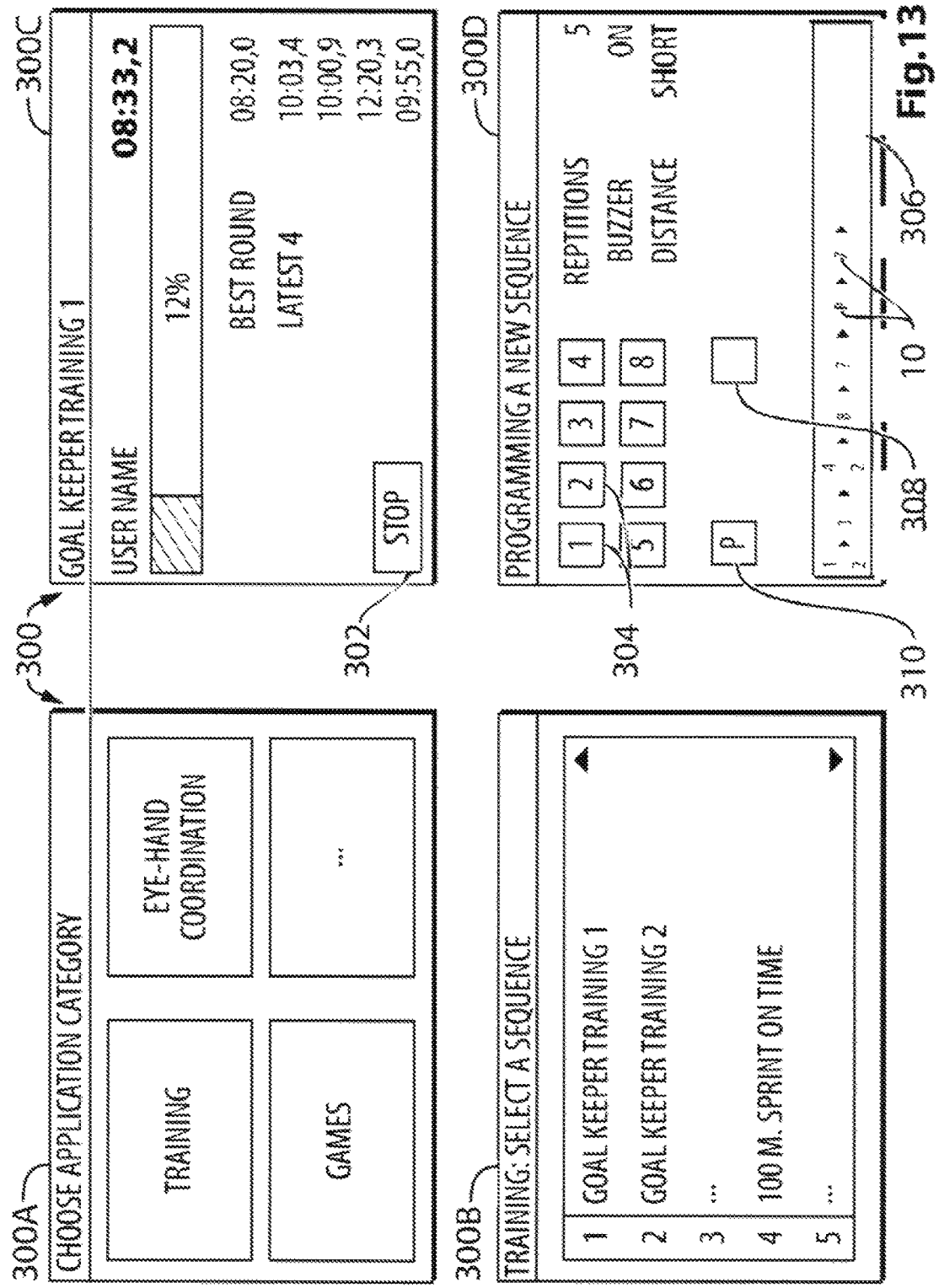
FIG. 13 is a series of screenshots depicting a graphical control panel provided by the system controller of FIG. 12 which may be used to program the exercise or training system.

FIG. 13 shows a graphical user interface 300 implemented on the system controller 200 and intended for display on its LCD screen 204. As exemplified in screen shot 300A, training routines are divided into different types of activities or groups for easy selection. As exemplified in screen shot 300B, each group contains a number of training routines or sequences. The training routine or sequence can be activated by pressing a virtual start/stop button 302. The name of the user performing the routine is preferably automatically known from a pre-assigned RFID tag 232 worn by the user. The performance metric(s) of the user are displayed in screen shot 300C.

Screen shot 300D shows how training routine or sequence can be programmed via a graphical control panel that utilizes the paradigm of a timeline. Each number button 304 represents a particular stimulant target unit 10. (Pressing on the number button 304 will cause the corresponding stimulant target unit to light up so that the user knows from a physical perspective which unit he or she is addressing.) By manipulating the number buttons 304 stimulant target units are added to a timeline 306. Multiple stimulant target units 10 can be addressed at a time as will be seen from the timeline 306. Arrow button 308 initiates the next step in the sequence. Alternatively, a pause can be inserted in the timeline 306 by pressing the P button 310. If desired, the control panel can request a numerical time value for the time delay between successive steps and/or the delay. The right side of the control panel screen also sets various options for the training sequence such as whether or not to use an audible feedback signal and the proximity distance required for the user to successfully actuate the stimulant target unit. These distances can be set as numerical values or more preferably through more intuitive labels such as "short", "medium", and "long" which will be translated by the control software into suitable numerical values.

In addition, the system provides another particularly desirable way of setting up a training routine or sequence by placing the system controller 200 in a learning mode. In this mode the user designates a sequence of stimulant target units by activating a specific unit(s), either by bringing his or her hand in proximity of the unit or by impact touching of the unit. The system controller 200 will then display a name, picture and/or geographical location of the unit and allow the user to enter the other data. For example, the system controller can place the designation number of the selected stimulant target unit in timeline 306. Additionally or alternatively, the system controller 200 can be placed in a full training or program mode where the users goes through a complete routine by activating the stimulant target units in a specific sequence and generating the timeline 306 based on such data. In this case, the system controller 200 receives feedback from the stimulant target units 10 as to the sequence of stimulant target units activated, the closest proximity distances (including zero) recorded by an activated stimulant target unit, and the time delay between successive activation of the stimulant target units. Once programmed, the systems controller 200 may iteratively speed up the sequence to make the exercise or training routine harder and harder for the user on each pass therethrough.

In addition, the system controller 200 may also accept a variety of global operating parameters that apply to an entire exercise or training sequence. This can include: a set next sequence time, programmable from 0 to 10 seconds in 1/10 second increments; and/or a default on-time, being the amount of time the light from the stimulant target unit is allowed to stay on before a 'miss' is registered, the on-time being programmable from 0 to 10 seconds in ⅒ second increments.

In addition to the programmed modes of operation discussed above, the system controller 200 may also operate in other modes. These include:

Random Mode. The system controller randomly signals stimulant target units 10 to light up.

Cognitive Mode. The target units 10 are turned on for "X" seconds (programmable) and then off and the user must identify the target units 10 that were activated in the pattern. For example, 8 target units 10 are turned on from a 10 light set up and the user must hit the ones that were not on or vice versa. This could also be done with a mixture of red and green lights or any combination of colours.

Linear Tracking Mode. The stimulant target units 10 follow each other linearly and the last one (or another as selected by the user) is triggered by the user in an anticipation drill. The speed of the movement between the stimulant target units 10 is programmable.

Total Light Mode. All stimulant target units 10 are on and the user must trigger them all off in a set time or non-set time. Both functions would be programmable.

Multi Light Mode: More than one stimulant target unit 10 comes on at the same time.

Randomized Speed Mode: The system continuously changes the rate of speed at which successive stimulant target units 10 light up thereby mixing up the rhythm of the user.

Linear Proximity Mode. The system decrements the deactivation distance for the stimulant target units 10 successively, or per successive exercise or training routine.

Randomized Proximity Mode. The system changes the deactivation distance for the stimulant target units 10 in random patterns, creating a degree of difficulty for the user that requires acute concentration and reaction awareness.

From the foregoing it should be appreciated that invention provides a universal fitness training system that can be applied to many areas of physical fitness, sport and high performance activities. The stimulant target units can be mounted on walls, floors or any apparatus that is used during training sessions to enhance the training and conditioning of the user. Additionally the stimulant target units can be mounted so as to simulate real sport specific situations, such as on tennis nets, squash courts, nets for volleyball or goal nets for, hockey, soccer etc. The system can be used for single person training, team training, passing route training, set play training, one on one, or team v. team. Endless routines and applications can be developed using the system, which is designed to be portable for all sports and conditioning activities.

Figure 14:
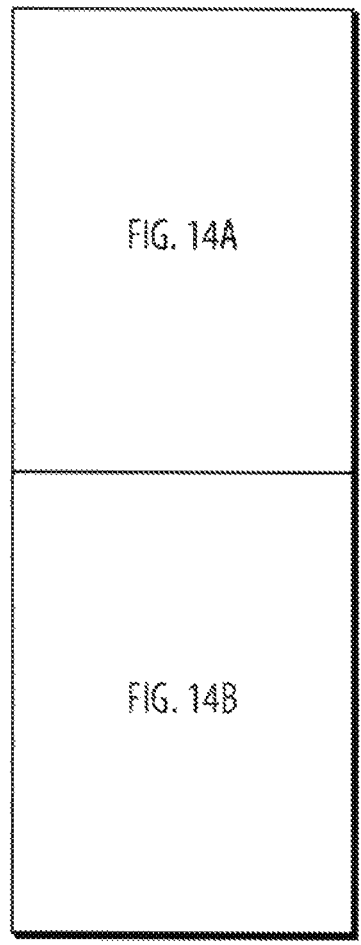
FIG. 14 schematically shows the relationship between the elements in FIG. 14A relative to the elements in FIG. 14B.
Figure 14A:
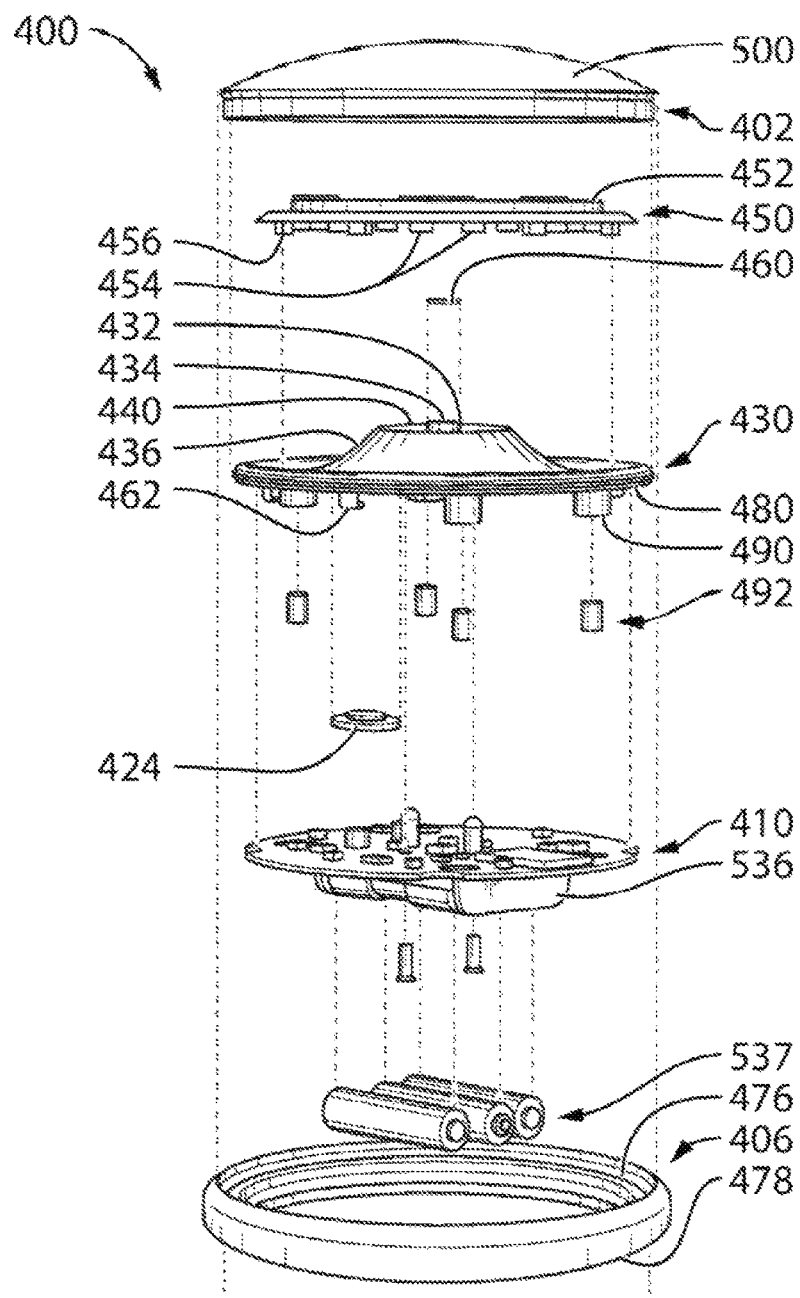
FIGS. 14A and 14B together are an exploded perspective view of a stimulant target unit according to a second preferred embodiment of the invention.
Figure 14B:
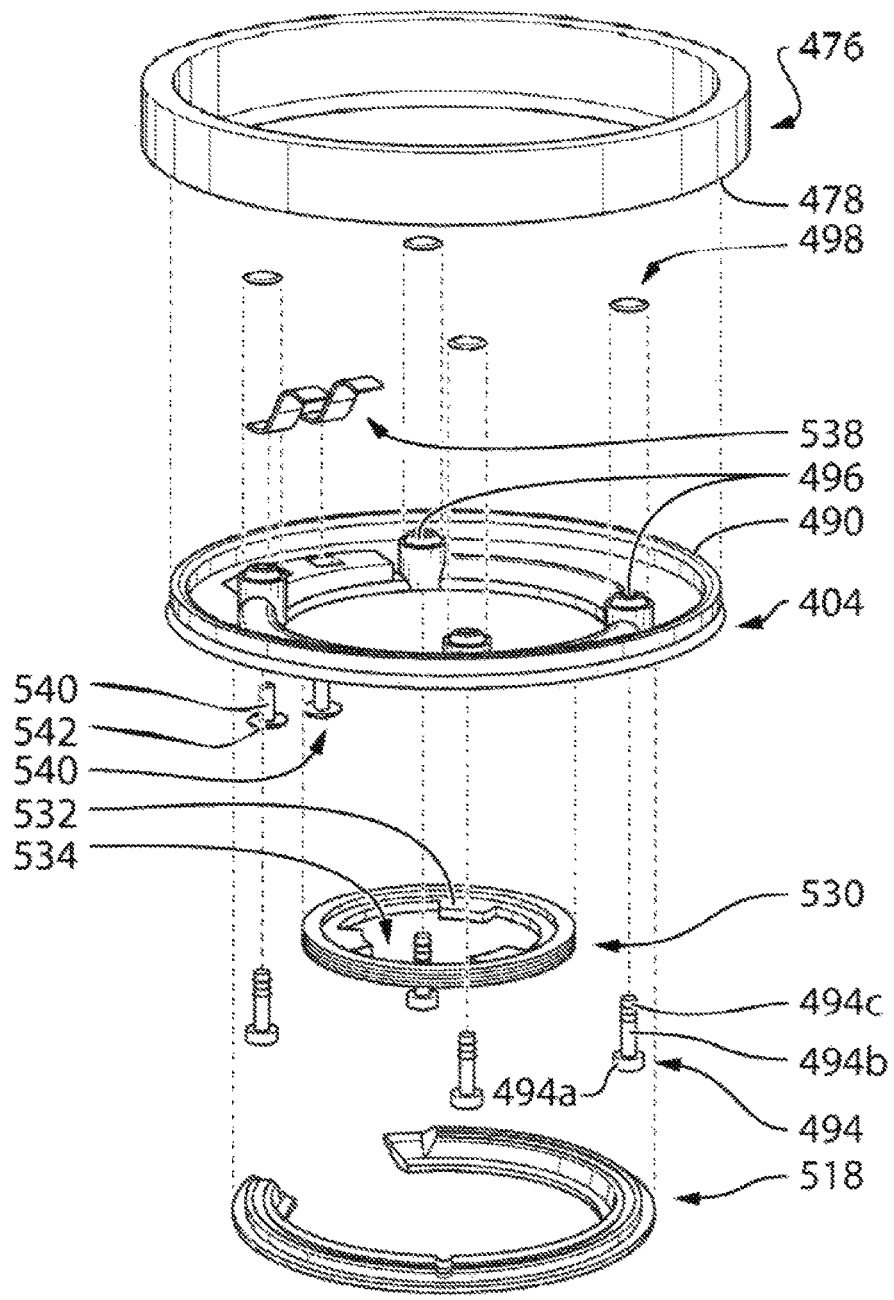

FIG. 14 shows an exploded view of a presently preferred stimulant target unit 400 that is particularly robust in its construction. The stimulant target unit 400 includes a translucent upper shell 402 and an opaque lower shell 404 which together form the majority of a housing. A rim 406 surrounds the upper and lower shells 402, 404 to join the two parts along their peripheries as discussed in greater detail below.

A printed circuit board (PCB) 410 is disposed in the housing between the upper and lower shells 402, 404. The PCB 410 carries circuit components for generating originating stimulus, measuring reaction or response time of the individual being exercised or trained, and generating feedback stimulus for the trainee to confirm that he or she has adequately responded to the stimulus. In the illustrated embodiment the PCB 410 carries a centrally located IR receiver 412, a surrounding inner annulus 414 of IR emitters 416 and surface mounted LEDs 418, and an outer annulus 420 of surface mounted LEDs 422. The inner annulus 414 may, for example, comprise two IR emitters 416 located 180 degrees apart and four LEDs 418 positioned along the inner annulus 414 in an "X" arrangement. The outer annulus 420 may, for example, include ten equidistantly spaced LEDs 422. The LEDs 418, 422 are preferably multi-coloured light sources in that their output colour may be controlled, as known in the art.

A speaker 424 may also be connected to the PCB 410.

Figure 15A:
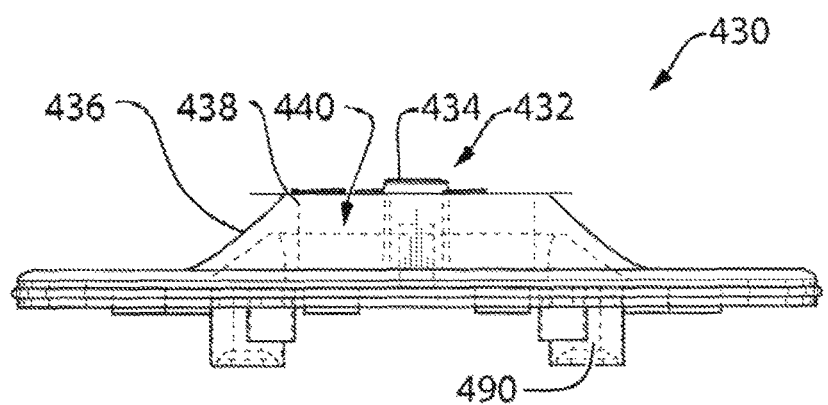
FIG. 15A is an elevation view of an inner cover utilized in the stimulant target unit of FIG. 14.
Figure 15B:
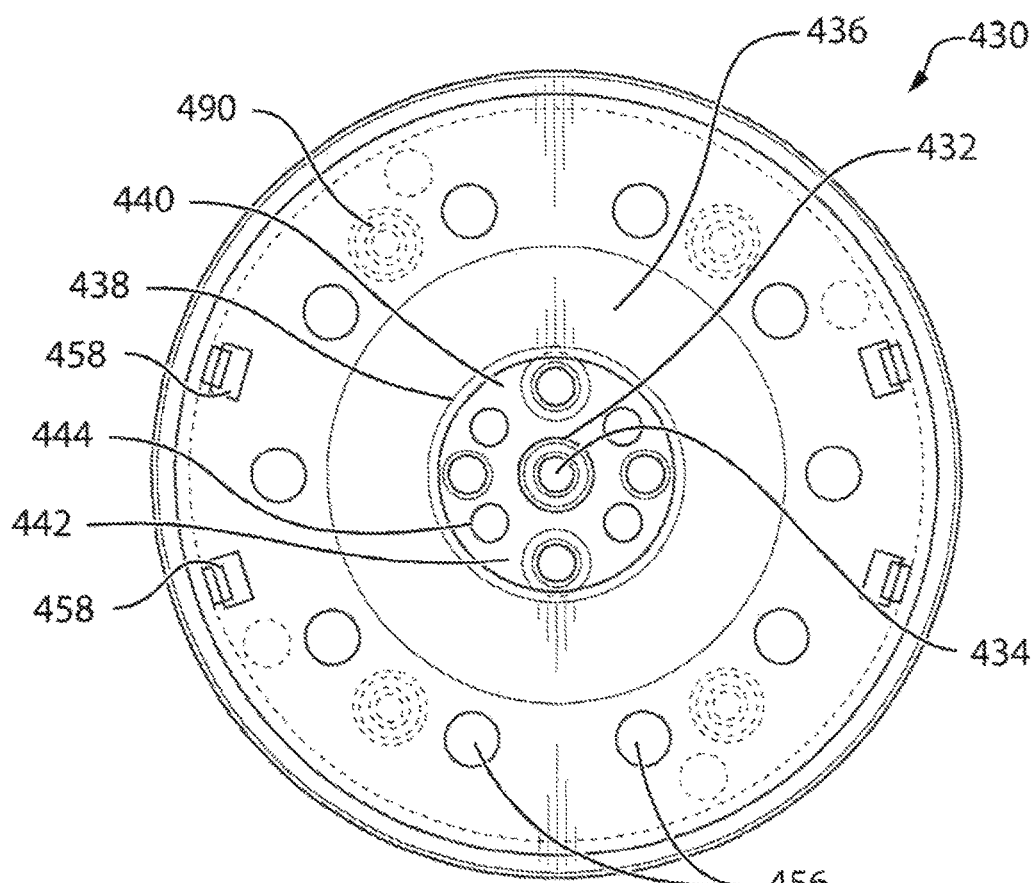
FIG. 15B is a top view of the inner cover shown in FIG. 15A.
Figure 16:
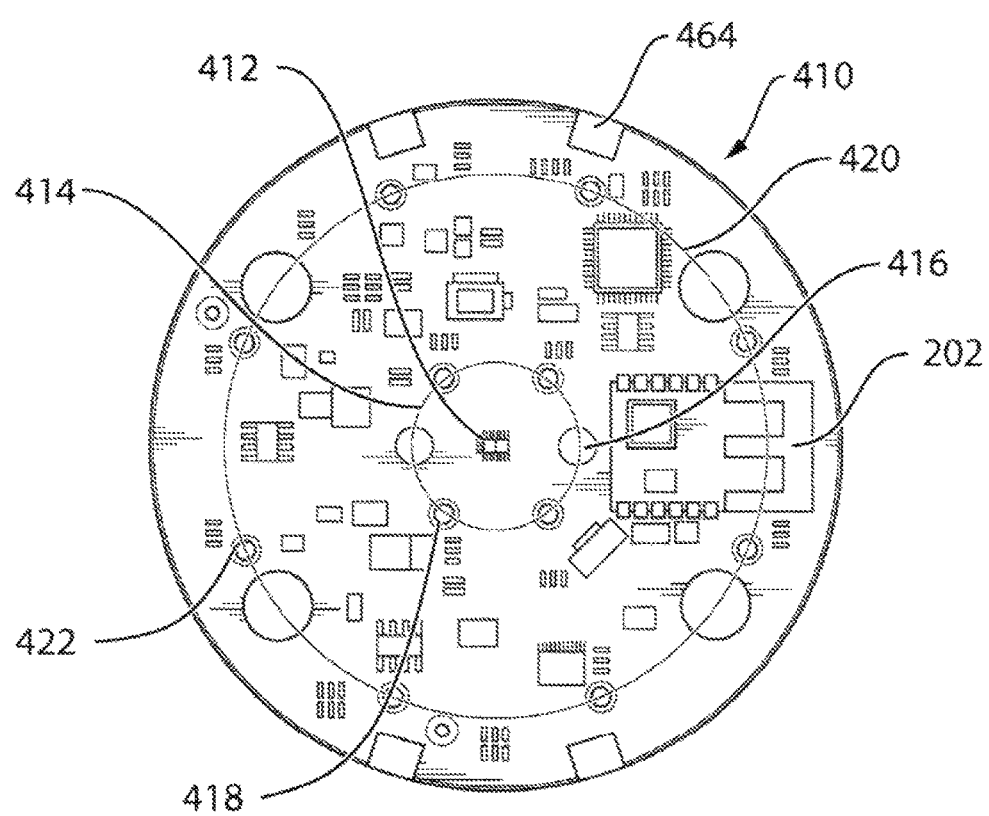
FIG. 16 is a plan view of a printed circuit board utilized in the stimulant target unit of FIG. 14.

An opaque inner cover 430 is positioned over the PCB 410. Referring additionally to the isolated elevation and tops views of the inner cover 430 shown in FIGS. 15A and 15B, the inner cover 430 has a central tube 432 having a central aperture 434 that registers with the IR receiver 412. The central tube 432 is surrounded by a frusto-conical shield 436 that has an inboard axial annular wall 438 with an elevation that is nearly or substantially equal to that of the central tunnel tube 432. Collectively the central tube 432 and inboard axial annular wall 438 form a toroidal tube or tunnel 440 coaxial with the central tube 432. The co-axial tunnel 440 has a radial floor 442 with a series of holes 444 therein that register with the components (IR emitters 416 and LEDs 418) of the inner annulus 414. Outboard of the frusto-conical shield 436 the inner cover 430 features an annular series of holes 446 arranged to coincide with the positions of the outer annulus LEDs 422 so that the light from these LEDs shine through the inner cover 430.

An annular light pipe or guide 450 is mounted atop the inner cover 422. The light guide 450 has an integrally formed ring 452 with downwardly projecting light guiding digits 454 that pass through the inner cover holes 446 to contact the surface mount LEDs 422. The digits 454 guide light from the LEDs 422 to the ring 452, which in turns distributes the light generated by the LEDs 422 around the ring 452 to thereby provide a more uniform ring-shaped light pattern as opposed to a series of point sources. This may make the stimulant target unit 400 more visible under sunny or bright conditions.

The co-axial tunnel 440, which preferably has walls that absorb light (and may for example, have a roughened surface texture) helps to reduce the spread of IR light emanating from the IR emitters 416 and direct the IR light along a more focused beam. The central tube 432, which preferably also has walls that absorb light and may include an inward taper or inward jog, helps to insulate the IR receiver 416, which is located at the bottom of the central tube 432, from stray light. In addition, an O-ring 460 is mounted between the central tube 432 and the upper shell 402 in order to reduce or eliminate any IR light emanating out of the coaxial tunnel 440 from leaking into the central tube 432. Individually and collectively, these features aid in creating a more accurate emission path and reducing the deactivation field, thus requiring the user to be more accurate in actuating the stimulant target unit 400.

The stimulant target unit 400 is constructed to withstand considerable forces and stresses. The components are interconnected as follows:

The light guide 450 connects to the inner cover 430 by a number of resiliently deformable clips 456 integrally formed on the underside of the light guide 450 that snap into mounting holes 458 formed in the inner cover 430.

The PCB 410 connects to the inner cover 430 via a number of resiliently deformable clips 462 integrally formed on the underside of the inner cover 430 that snap into rebates 464 formed along the outer periphery of the PCB 410.

The inner cover 430, having the flight guide 450 and PCB 410 attached thereto, also connects to the upper shell 402 via a snap fit. Referring additionally to the detail assembly cross-section view of FIG. 17, the inner cover 430 has an outer peripheral reinforcing flange 470 that is downwardly tapered on its top surface. The outer flange 470 joins a straight outer sidewall 472 with an integrally formed projecting snap ring 474. The upper shell 402 has an axially extending circumferential flange 480 with a complementary shape along the inner diameter thereof. The complementary shape includes an annular rebate 482 sized slightly smaller than the snap ring 474 so that the snap ring 474 locks (releasably) into the annular rebate 482 of the resiliently deformable axially extending circumferential flange 480.

Referring to FIG. 14, the upper shell 402, having the inner cover 430, light guide 450 and PCB 410 attached thereto as hitherto described, is suspendingly connected to the lower shell 404 via the rim 406, which is formed from an elastomeric material such as rubber. The rim 406 features an upper annular groove 476 and a lower annular groove 478. The upper shell axially extending circumferential flange 480 seats in and along the rim upper annular groove 476. The lower shell 404 has an axially extending circumferential flange 490 that seats in and along the rim lower annular groove 478. The inner cover 430 has a series of mounting cavities 490 integrally formed on the underside thereof. Threaded socket inserts 492 are fixed (e.g., via thermal bonding) in the mounting cavities 490. (The mounting cavities 490 could alternatively be constructed with integrally formed threaded sockets.) Carriage bolts 494, each having a head 494a, a smooth shaft 494b proximate the head and a threaded shaft 494c distal the head, are passed through mounting bores 496 formed in the lower shell to fasten together the lower shell 402, rim 406, and inner cover 130/upper shell 402 assembly. (O-rings 498 may be disposed between the mounting bores 496 and the PCB 410.) This manner of connection enables the upper shell 402 and lower shell 404 to move axially relative to one another when, for example, the upper shell 402 is impacted and deforms the elastomeric rim 406.

Figure 17:
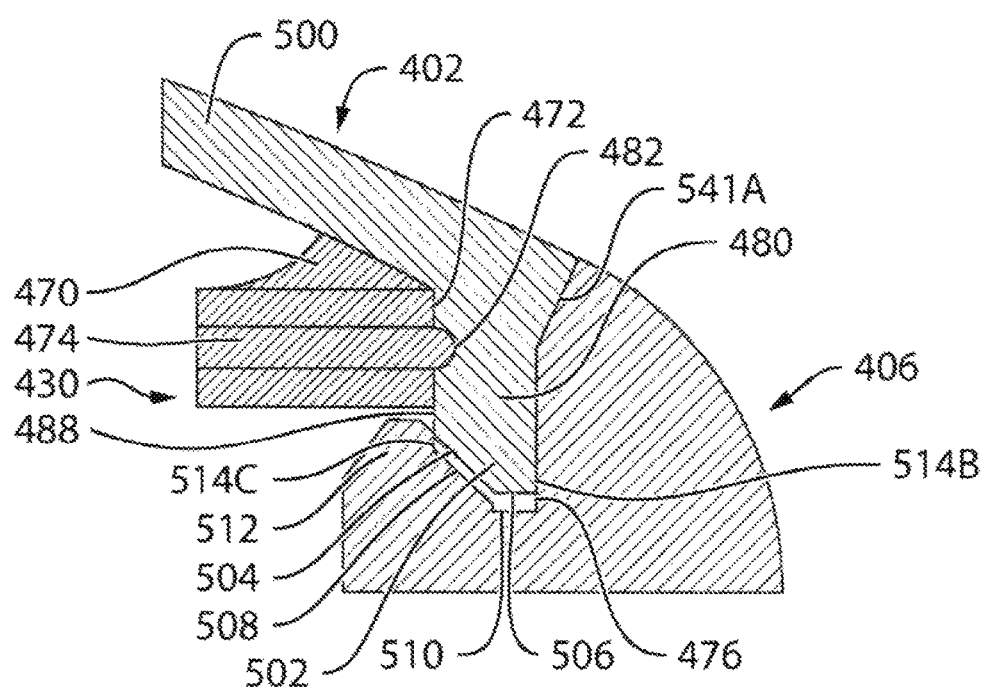
FIG. 17 is a detail cross-section view of a portion of a housing utilized in the stimulant target unit of FIG. 14.

The detail view of FIG. 17 provides more detail on how impact forces are handled by the stimulant target unit 400.

The translucent upper shell 402 is preferably formed from an impact resistant polymer such as polycarbonate. The upper shell 402 is domed-shaped, having a semi-spherical top surface 500 (which is semi-circular in cross-section). The upper shell axially extending circumferential flange 480 has an outboard face 484 that is matched by an outboard wall 486 of the rim upper groove 476 and an inboard face 488 that is partially met by an inboard wall 489 of the rim upper groove 476. The upper shell axially extending circumferential flange 480 also has a bottom portion 502 with a canted wall 504 joining a flat end face 506, however, the bottom portion 502 does not fully seat into the complementarily shaped canted 508 and bottom walls 510 of the rim upper groove 476, i.e., there is normally a space between walls 504, 508 and 506, 510. The domed shape of the upper shell 402 helps to transfer impact forces to the outboard periphery thereof. The force will have an axial component and a transverse component. The transverse component of the force will be resisted by the outboard wall 486 of the rim 406. The axial component of the force will drive the axially extending circumferential flange 480 downward to be resisted by the canted and bottom walls 508, 510 of the rim upper groove 476. In the process, the bottom portion 502 of the axially extending circumferential flange 480 could deflect or deform an inboard finger portion 512 of the rim 406.

The axially extending circumferential flange 490 of the lower shell 404 is similarly shaped and installed in the similarly shaped rim lower groove 478, which provides the lower shell 404 with room to move relative to the rim 406.

As seen best in FIG. 17, the foregoing construction provides a three point seal at 514a, 514b and 514c between the upper (or lower) shell 402 and the rim 406, which is effective in enabling the stimulant target unit 400 to be water resistant and used under wet conditions such as in the rain or in swimming pools. The domed shape of the upper shell 402, having its most elevated region over the IR emitters and receivers 412, 416 also aids in directing water that would otherwise interfere with the sensors away from the sensors so that the stimulant target unit 400 can be used in wet conditions. Alternative embodiments may use other shapes instead of a dome to allow water to flow away from the IR sensor, such as pyramidcal or conical.

Figure 18:
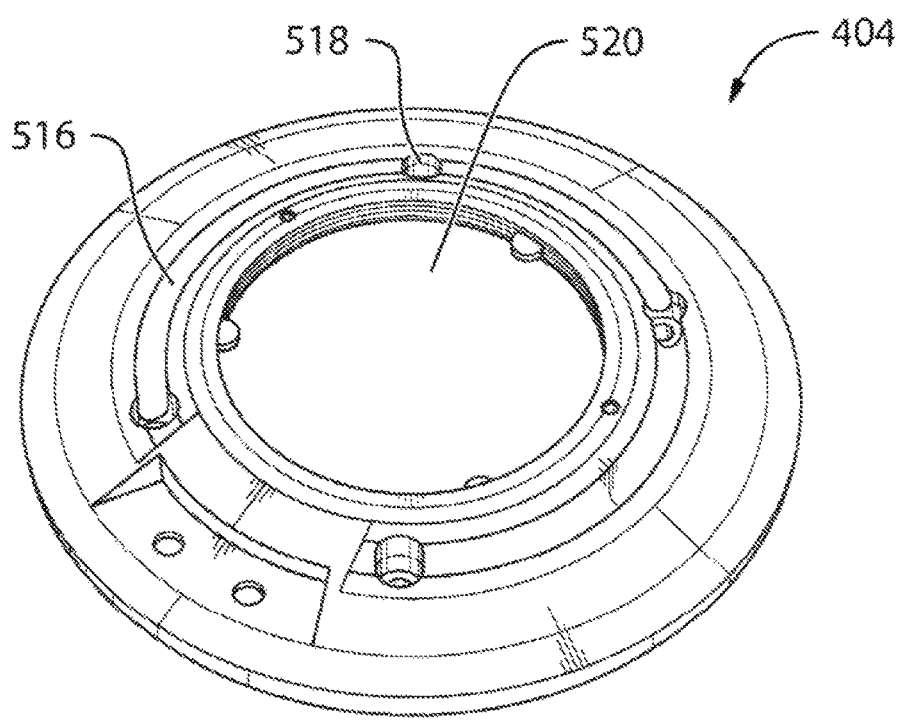
FIG. 18 is a bottom perspective view of a shell used in the housing of the stimulant target unit of FIG. 14.

Referring additionally to the bottom perspective view of the lower shell in FIG. 18, the lower shell 404 has a semi-circular groove 516 having holes 518 therealong through which the carriage bolts 494 are passed. The bolt heads 494a seat within the groove 516 so as not to be exposed. An elastomeric seal 518 (FIG. 14) is provided to cap this groove 516.

The lower shell includes a cavity 520 on an underside thereof to which a lock member 530 is mounted. The lock member 530 includes a plurality of radially oriented lugs 532 and intervening rebates 534 which are collectively intended to inter-engage with corresponding features of a mating lock member on a mounting accessory such as 50 or 60.

The underside of the PCB 410 has a battery compartment 536 mounted thereon for holding preferably replaceable rechargeable batteries 537. The lower shell 404 has two leaf springs 538 mounted thereon that are disposed to contact relatively large electrically conductive pads (not shown) on the underside of the PCB 410 that are electrically connected to the batteries. The leaf springs 538 are riveted to the lower shell 404 by rivets 540 have electrically conductive heads 542 which provide external charging ports that can be used to recharge the batteries in the compartment 536 without having to remove the batteries.

The stimulant target unit 400 utilizes electronic circuitry similar to that described with reference to FIG. 10. The proximity sensor is an IR sensor provided by the IR emitters and receiver 416, 412, as previously described, and the microprocessor 202. (The stimulant target unit 400 also employs an accelerometer to register physical contact and/or force as discussed above.) The IR proximity sensor is preferably configured to operate in one of two modes: a 'normal' mode and an 'racket' mode.

Figure 19:
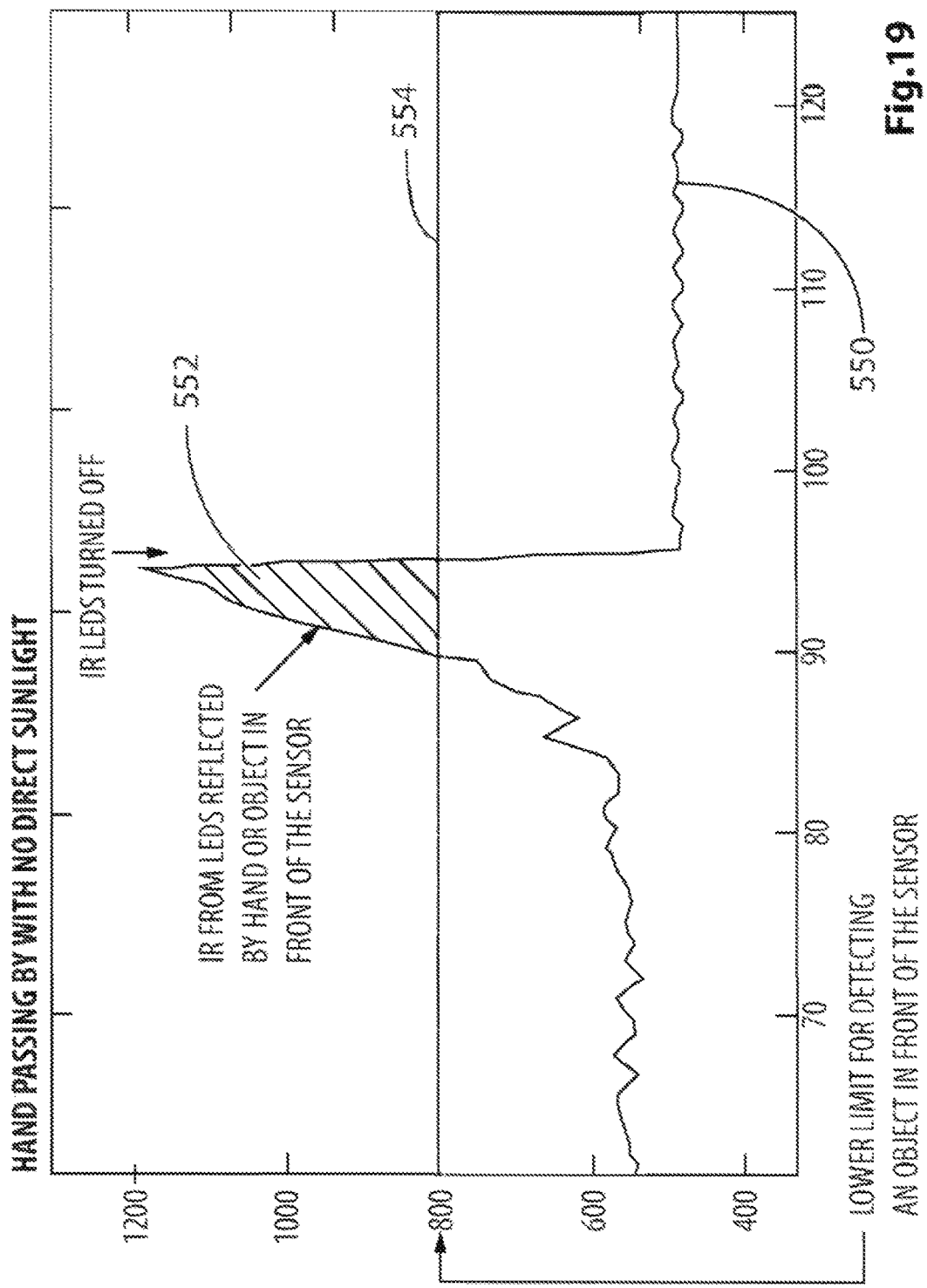
FIGS. 19, 20 and 21 are graphs depicting three different object detection algorithms, respectively, employed by an infra-red sensor utilized by the stimulant target unit of FIG. 14.

In the normal mode, the IR sensor operates in one of two selected sub-modes depending on the ambient IR level, a non-direct sunlight sub-mode and a direct sunlight sub-mode. As seen in FIG. 19, when the stimulant target unit 400 is indoors the ambient IR level will be below a threshold. When the user's hand or other object passes in front of the IR beam IR light will be reflected off the hand or object and picked up by the IR receiver 412, causing the detected IR level to increase as seen at portion 552 of the IR level vs. time plot 552. To verify the object detection, the microprocessor 202 turns off the IR emitters 416 after an IR detection threshold level 554 is crossed. If the detected IR level reverts back to below the threshold 554, then the IR proximity sensor registers an object detection. Note that the microprocessor 202 may rapidly cycle the IR emitters 416 on and off in this sub-mode in which case the plot 550 represents the detected IR level when the IR emitters 416 are on.

Figure 20:
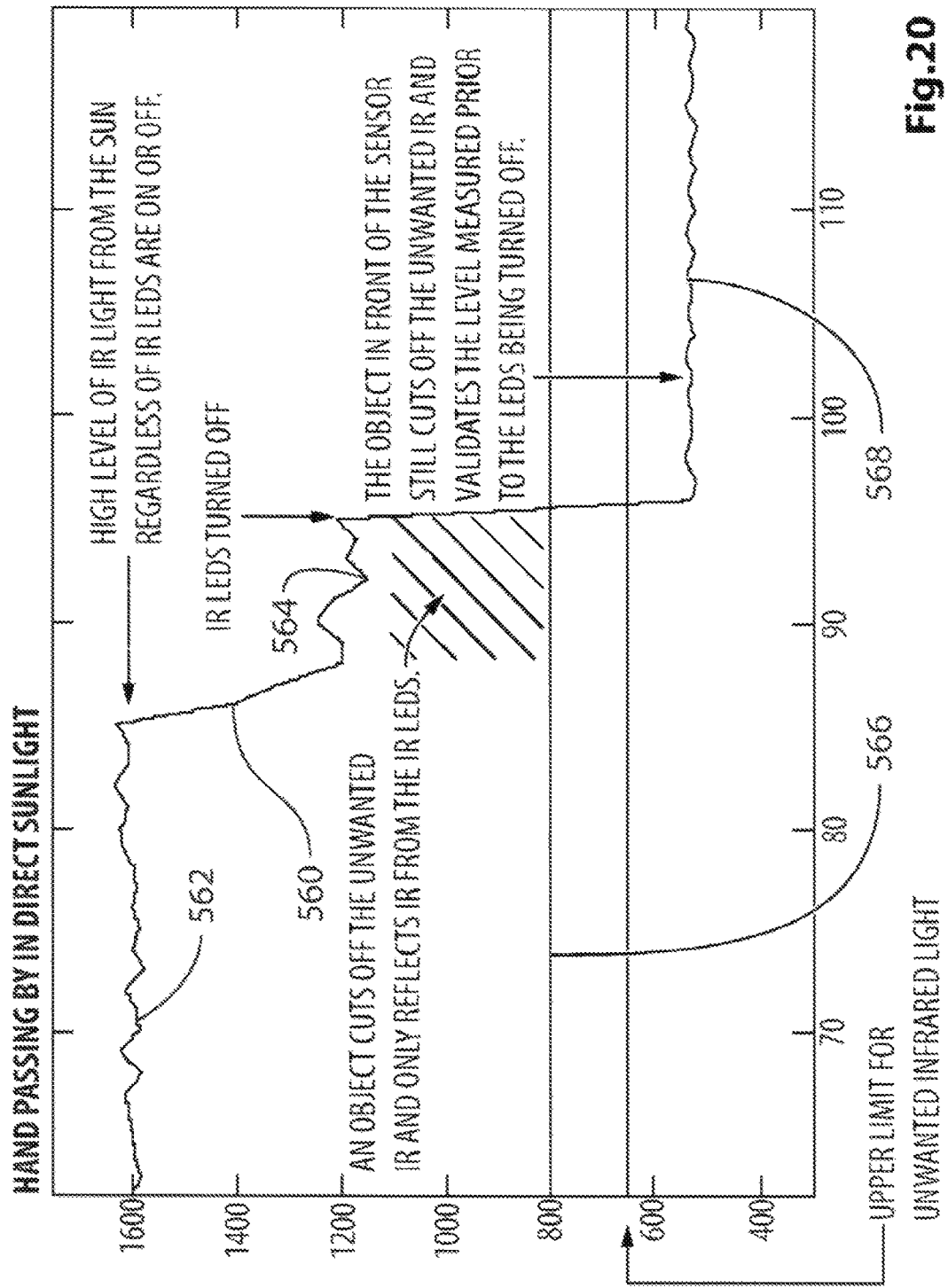

FIG. 20 shows a plot 560 of detected IR level against time under sunny conditions. In this case, as indicated by portion 562 of the plot 560, the ambient IR level is relatively high irrespective of whether or not the IR emitters 516 are on or off. However, as seen by portion of 564 of the plot 560, when a hand or other object is placed in front of the IR receiver 412 the detected infrared light due to the sun is blocked resulting in a lower IR reading but one which is still above a threshold level 566. To verify the object detection, the microprocessor 202 turns off the IR emitters 416 and looks to see that the IR level has decreased, as at plot portion 568, below the threshold 566. The verification strives to ensure that the reason the IR level decreased at portion 564 is due to a reflection from the IR emitters 416 and not due to a temporary reduction in the ambient IR light levels. The microprocessor 202 may also rapidly cycle the IR emitters 416 on and off in this sub-mode in order to carry out this detection algorithm.

In the 'normal' mode the IR proximity sensor discerns the proximity of the hand or other object based on the peak levels of detected IR light at portions 552 or 564.

Figure 21:
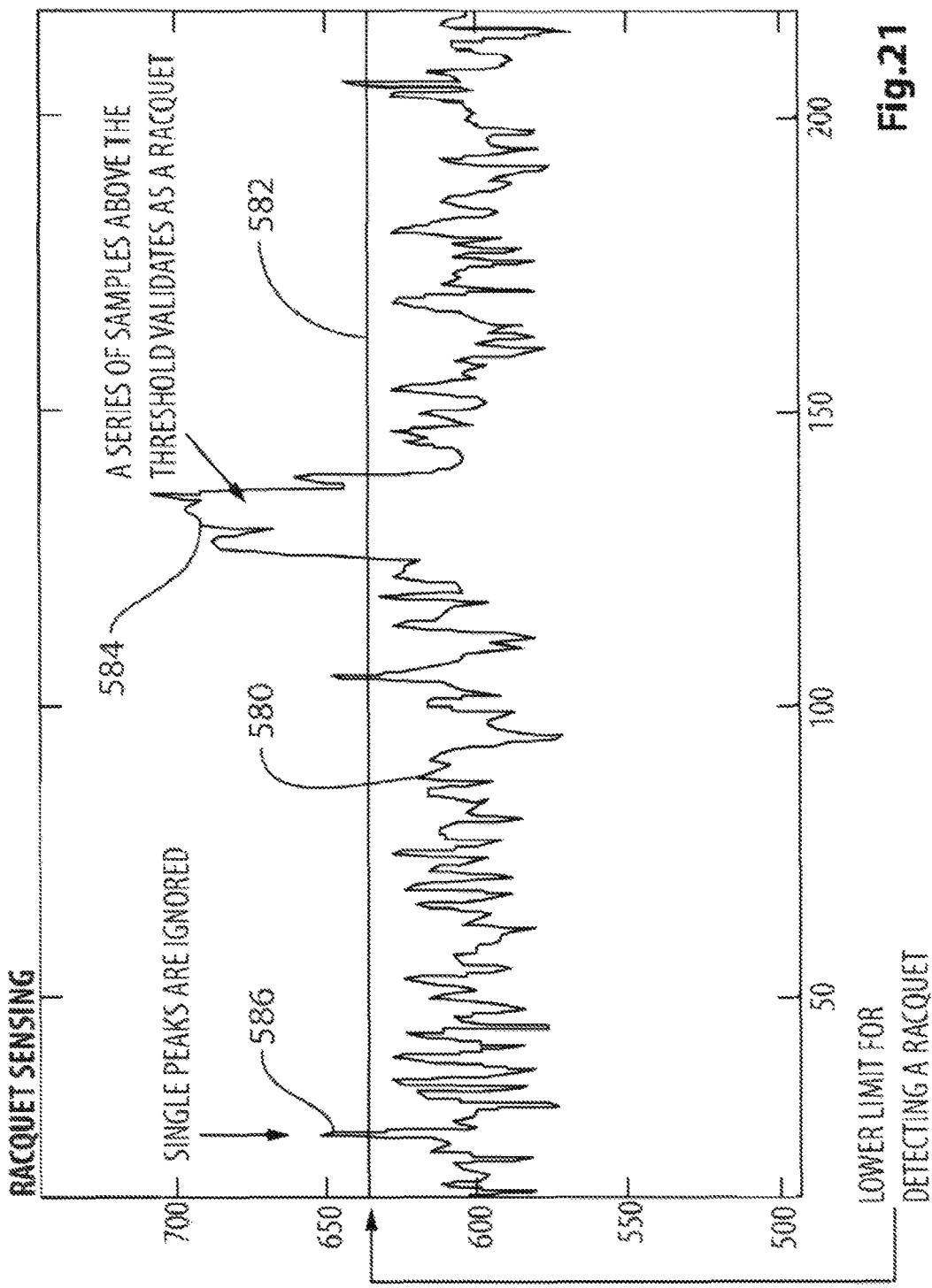

FIG. 21 shows a plot 580 of detected IR level against time in the 'racket' mode. In this mode the IR proximity sensor operates at a relatively high sensitivity as seen by the relatively high ripple in the plot 580. A racquet typically has very thin strings which are difficult to detect but it will be appreciated that the racket frame is comparatively thicker and will disrupt the IR beam when a person moves the racket to actuate the stimulant target unit 400. In order to detect the racket frame, the microprocessor 202 looks for an IR reading, such as at portion 584, that is greater than a threshold level 582 (which is comparatively lower than threshold levels 554 or 566 and closer to ambient levels) for a minimal period of time. The microprocessor 202 may rapidly cycle the IR emitters 416 on and off in this mode, for example, at a few hundred cycles per second, and the minimal period of time may be, for example, about 6 to 10 consecutive cycles. Isolated peaks such as at plot portion 586 above the threshold 582 are ignored.

If desired, the different modes of operation (sunny, no sun, and racquet) may be specifically selected by the user.

The stimulant target unit 400 may be controlled along with like units by an electronic control system 600 similar to that shown in FIGS. 11-12, including a system controller 602. FIGS. 22-40 show input screens generated by a presently preferred graphical user interface (GUI) provided by the system controller 602. FIG. 41 provides a key illustrating how the input screens are ordered relative to one another.

Figure 22:
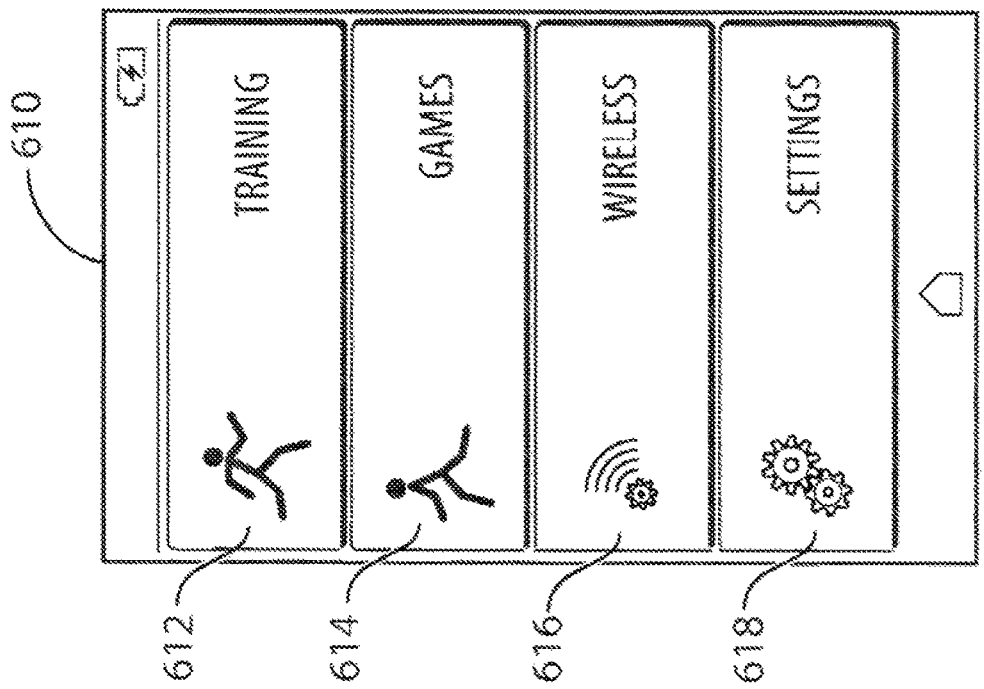
FIG. 22 shows a main input screen with icons representing menu items based on function.

FIG. 22 shows a main input screen 610 with four icons representing four menu items based on function: Training 612, Games 614, Wireless 616 and Settings 618. The Training function 612 utilizes the stimulant target units 400 in various training configurations described below. The Games function 614 permits one or more users to utilize the stimulant target units 400 in one or more different types of games. The Wireless function 616 configures the stimulant target units 400 in one or more groupings. The Settings function 618 controls various user adjustable settings.

Figure 23:
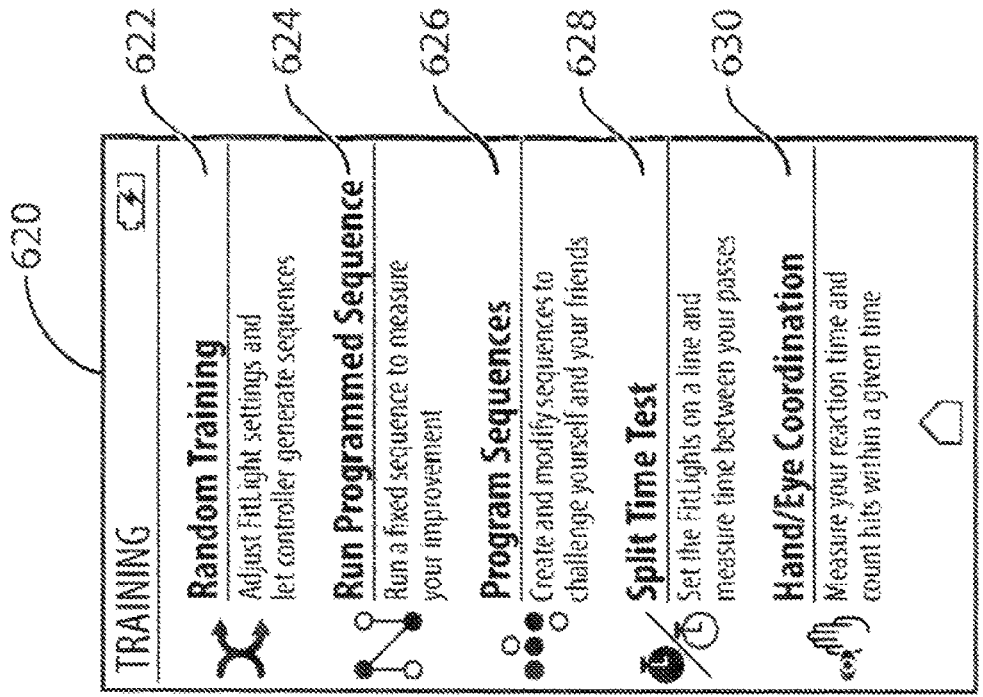
FIG. 23 shows a secondary input screen displaying icons representing different training functions.

FIG. 23 shows a secondary main input screen 620 with five icons representing five different kind of training functions: Random Training 622; Running a Programmed Sequence 624; Program(ming) Sequences 626; Split Time Testing 628; and Hand/eye Coordination 630.

FIGS. 24 to 26 show the input screens associated with the Random Training function 622. In the random training function, the system controller randomly stimulates the system stimulant target units 400, and the person being trained has to actuate the specific units that have been randomly stimulated.

FIG. 24 shows an input screen 632 having various fields that the user can adjust (and which will be implemented by the system). The fields include a proximity Distance, Hits, Timeout, Delay, Color, and Penalty. The Distance field specifies the distance by which the trainee's hand or other object must approach the unit 400 in order to register a successful actuation thereof. A zero distance indicates that trainee must physically touch the unit 400 (which is equipped with an accelerometer for this purpose as previously described) in order to register an actuation. The Hits field specifies the length of the sequence, for example, 50 Hits will cause the system controller to randomly illuminate the units 50 times. The Timeout field specifies the maximum length of time that the system will wait for the trainee to actuate a presently stimulated unit 400 until the next unit 400 is stimulated. The Delay field specifies the time between the actuation of one unit 400 and the onset of the stimulation of the next unit 400 in the sequence. For example, with a 0.5 second delay the next unit would be illuminated ½ second after a presently illuminated unit is actuated by the trainee. The Color field enables the user to specify the color of light generated by the LEDs 416 and/or 422. The Penalty characteristic may be deactivated or turned off (as illustrated). When activated, the Penalty adds an indicated penalty time to the user timer statistics as discussed in greater detail below.

The '+' and '−' icons next to each field enables the user to change the value of the field in discrete steps or to select a following item in an enumerated list, for example, to change the Distance by a 5 cm increment or change the Delay by a 0.1 second increment. Actuating a 'reverse' icon 634 causes the system controller to display the previous input screen and actuating a 'home' icon 636 causes the system controller to display the main input screen 610.

FIG. 25 shows additional settings or fields that the user can adjust (and which will be implemented by the system) through various check boxes. These fields include: a Beep field, which specifies whether or not the units 400 generate a sound when stimulated; a Start by Light field, which specifies whether or not the random sequence starts only when the trainee actuates a first illuminated unit 400; a Record Stats field, which specifies whether or not to record various performance statistics in on-board memory; a mutually exclusive series of check boxes 644 which specify how the LEDs of the unit 400 are to be illuminated, either with a quick Flash, Permanent (continuous illumination), a continuous Slow Blink, or a continuous Fast blink; a mutually exclusive series of check boxes 642 which specify the light annuli that are illuminated, wherein Center Only specifies illumination of the inner annulus 414, Ring Only specifies illumination of the outer annulus 420, and Full Light specifies illumination of the inner and outer annuli 414 and 420; and a mutually exclusive series of check boxes 646 which specify whether or not actuation of the unit 400 is registered through proximity sensing (Distance), by physical Impact, or via proximity sensing and impact.

FIG. 26 is a performance screen 648 for the random sequence function, in which a variety of counters or timers are displayed that measure various performance criteria once the process starts following activation of a 'start' icon 650. Icon 652 indicates the active groups of unit 400, as discussed in greater detail below. (In the illustrated screen of FIG. 26 there is only one group labelled 'A', and one set of counters and timers per group). Counter 652 displays the sequence number. Timer 654 displays the total time that the sequence is/has taken. Counter 656 displays the number of timed out units 400, i.e., units that the trainee has not successfully actuated within the time period specified by the Timeout field. Timer 658 specifies the trainee's reaction time (from the instant the unit 400 informs the system controller that the unit 400 has been stimulated until the instant that the trainee has actuated the stimulated unit 400 or until the Timeout period has elapsed, whichever comes first). This timer 658 eliminates the Delay time from the count (whereas Timer 654 includes the Delay time), but if a Penalty is specified then the penalty period is added to the count in the event the trainee does not actuate the stimulated unit within the Timeout period. Timer 660 displays the trainee's average reaction time in actuating the units 400.

FIGS. 27 to 29 shows the input screens associated with the programmed sequence training function 624. In the programmed sequenced training function the system controller stimulates the stimulant target units 400 of the system in a pre-ordained sequence, and the trainee has to actuate the units in order of the selected sequence. FIG. 27 shows an input screen 652 which enables the user to select a predetermined sequence (Seq No) and to specify how many times the selected sequence should be repeated. FIGS. 28 and 29 show input and performance screens similar to those of FIGS. 25 and 26 and will be understood with reference to the discussion above.

FIGS. 30 to 33 show input screens for the programming sequences function. These are the sequences utilized in the sequence training reference by FIGS. 27 to 29. FIG. 30 shows an input screen 658 that enables the user to select a sequence number that will be further defined in the input screens of FIGS. 31 to 33. FIG. 31 shows an input screen 660 that enables the user to specify two different settings, Setting 1 and Setting 2. Each setting is associated with Distance, Timeout, Delay and Color values, as discussed above. FIG. 32 shows an input screen 662 that enables the user to associate each individual unit 400 with one of the two settings. FIG. 33 shows an input screen 664 that enables the user to specify the sequence of units 400. The screen utilizes a table 666 with columns 668. Each column 668 specifies the specific units 400 that are to be stimulated simultaneously, and consecutive columns specify the sequence. Thus, using the data illustrated in FIG. 33 as an example, the sequence starts out by stimulating unit nos. 6, 7 and 5, then unit no. 3, then unit nos. 3 and 6, then unit nos. 2 and 7. The input screen 664 also enables the user to specify additional delays between sequence iterations. For example, using the data illustrated in FIG. 33, a delay of 0.1 seconds has been interjected after the fourth iteration where unit nos. 2 and 7 are to be stimulated. The 'save' icon 670 saves the foregoing to memory.

FIGS. 34 to 35 showing input and performance screens associated with the split time function. FIG. 34 shows an input screen 672 which enables the user to specify Distance and Color values, as discussed above. There is no Delay or Timeout in this exercise. FIG. 35 shows a performance screen 674 for the split time function. Here, the system controller illuminates each unit 400 in sequence of its unit number. This allows the user to set up the units 400 linearly (or in some other order as desired). Once the process is initiated via the start icon 675, the system measures and displays time periods 676 between successive actuations of stimulated units 400.

Figures 36, 37:
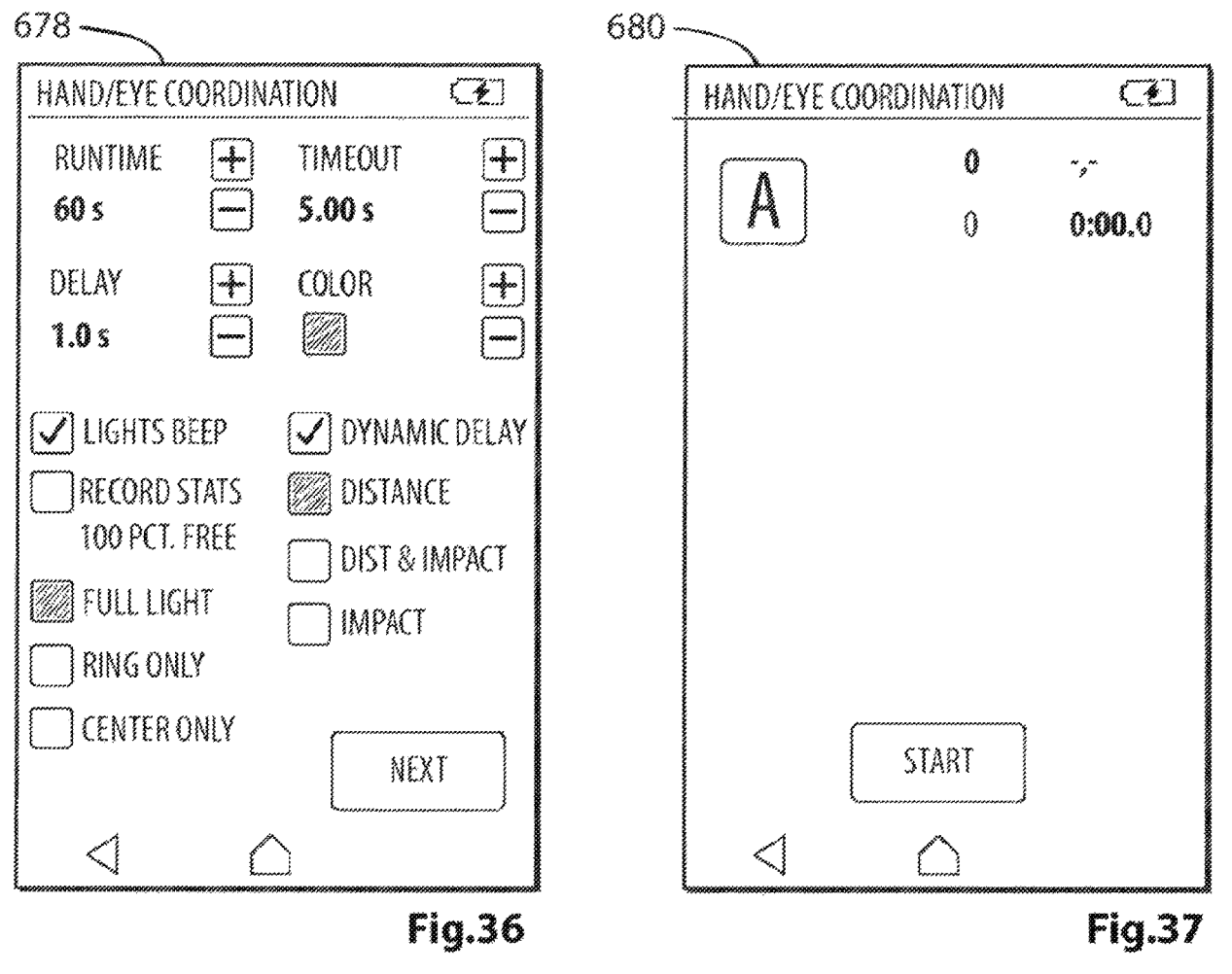

FIGS. 36 and 37 show input and performance screens associated with the hand/eye coordination function. FIG. 36 shows an input screen 678 which enables the user to specify a total run time (Runtime), as well as Timeout, Delay and Color values as previously discussed. The input screen 678 also allows the user to specify the type of illumination and the type of action necessary for registering an actuation of the units, as previously discussed. In addition, the input screen 678 enables the user to check off a Dynamic Delay box, in which case the system will randomly delay the time between successive stimulation of the units 400. FIG. 37 shows a performance screen 680 similar to those previously discussed.

The Games function 614 shown in FIG. 22 provides the user with access to various games. For example, in one game, the system controller divides the units 400 into two groups. The groups are identified by differently coloured lights. The game requires two or more individuals to race against each other to see who can more quickly actuate the units associated with their group. In another game, the units are likewise divided into two groups. Actuating a unit in one group cause the stimulation of a unit in the other group. A variety of other games may be played.

Figure 39:
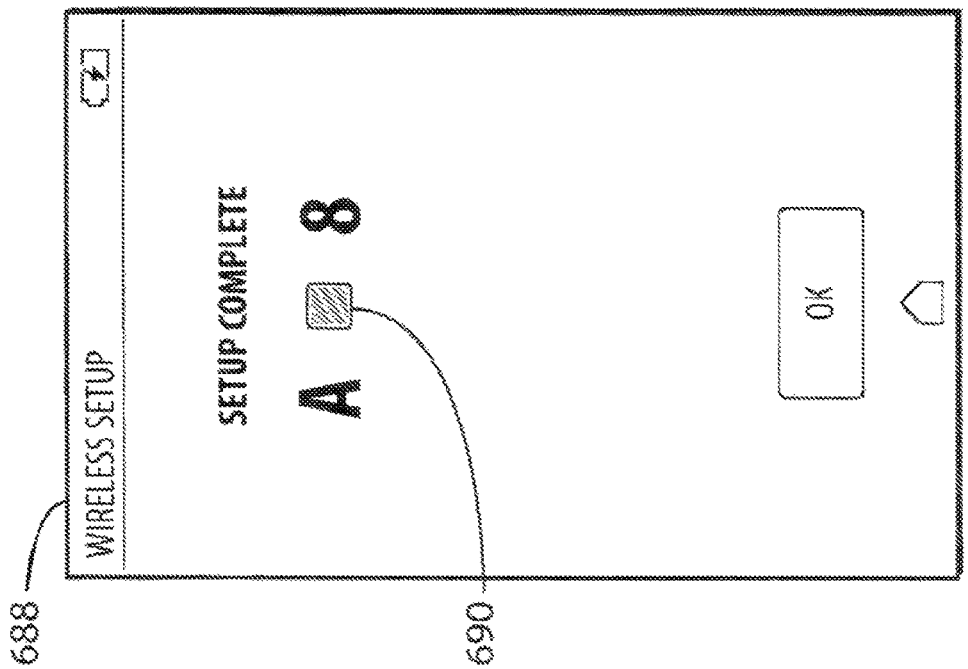
FIG. 39 shows a performance display screen relating to the Wireless function that is displayed when a first check box is checked on the screen shown in FIG. 38.
Figure 38:
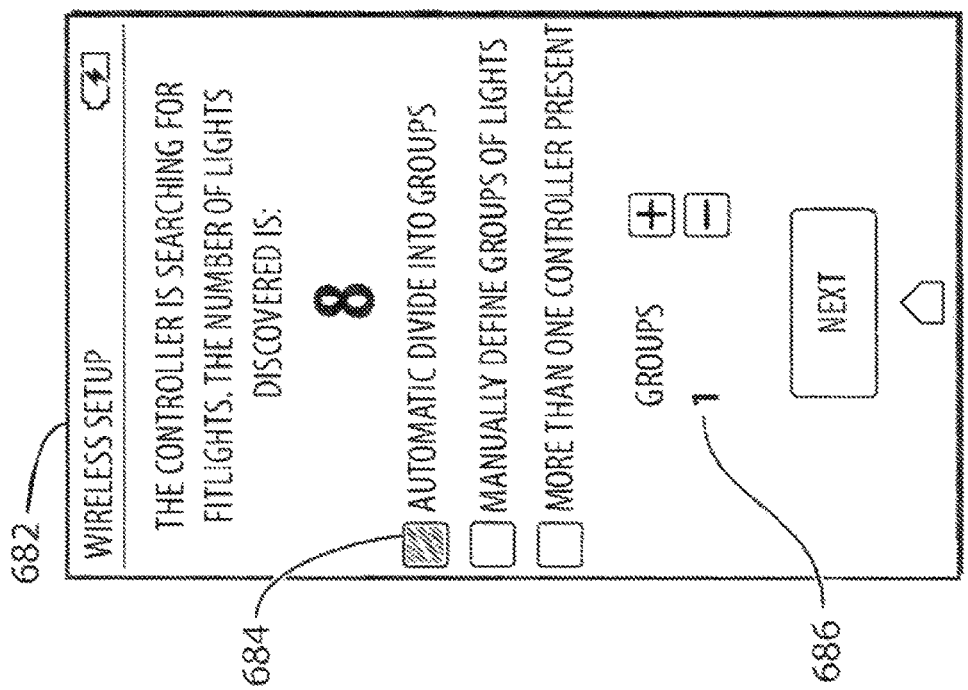
FIG. 38 shows an input screen displaying icons relating to a Wireless function.

The Wireless function 616 shown in FIG. 22 allows the user to bifurcate the units 400 into one or more groups. FIG. 38 shows an input screen 682 for the wireless function, which displays mutually exclusive check boxes 684 that enables the user to: in a first check box, automatically divide the units 400 into groups; in a second check box, manually define groups of units 400; and in a third check box, associate the units 400 with more than one system controller if it is present. The input screen 682 also includes a field 686 enabling the user to specify how many groups he or she wants. FIG. 39 shows a performance screen 688 when the first check box is selected. Here, the system automatically divides the unit 400 into one or more groups labeled A, B, C . . . . In the illustrated example all eight of the units 400 are assigned to one group labeled 'A'. Once the units are assigned to a particular group the system controller associates each group with a different colour as displayed bi color block 690 and illuminates the units 400 in accordance with the associated group colour so that the user can identify which unit 400 belongs to which group. FIG. 40 shows an input screen 692 that is displayed when the second check box is selected. In this case the system controller illuminates all the units 400 with one color and requests the user to select/actuate those units which will be assigned to the highlighted group label. When the user makes his or her selection the actuated units will change colour so that the user those which units belong to the group. To assign units to the next group, the user selects an icon 694 representative of the next group and repeats the process. The selected units associated with the second group will thereafter change to a colour that is different from the initial color and the color of the first group. The process may be repeated to assign various units to various groups.

The Settings function 618 shown in FIG. 22 enables the user to adjust various user adjustable setting such as the brightness of the system controller display, erasing the memory, and resetting the system to initial default states. In addition, the Settings function may optionally include a false start indicator. The proximity sensor employed by each unit 400 can sense the change in distance to the trainee's hand or other object. When the distance reduces, the unit 400 determines that the hand or other object is approaching the unit. Conversely, when the distance increases the unit 400 determines that the hand or other object is receding from the unit.

In the event a unit 400 is stimulated and the proximity sensor immediately detects a receding object, or detects a receding object but has not detected an approaching object, a determination may be made that there has been an false start and the system controller may display an indication of such in any of the foregoing performance screens.

Those skilled in the art will appreciate that a variety of modification may be made to the embodiments discussed herein without departing from the scope of the invention as defined by the appended claims.

The invention claimed is:

1. An exercise training system, comprising:
   a system controller;
   a plurality of stimulant target units connected via a wireless network to the system controller, each stimulant target unit including a housing, a light source providing light to stimulate a user, a proximity sensor providing an output of a distance between the proximity sensor and an object external to the stimulant target unit, an impact sensor mounted in the housing, and feedback means for informing the user that the stimulant target unit has been actuated;
   wherein each stimulant target unit further includes a power source and a stimulant target unit controller that are separate from the power source and the stimulant target unit controller of each of the other stimulant target units, wherein the stimulant target unit controller for each of the plurality of the stimulant target units is wirelessly connected to the system controller and is programmed to receive instructions from said system controller, wherein the selected proximity distance required to actuate each stimulant target unit is programmable by the user;
   wherein the system controller includes a program for activating the stimulant target units in a sequence, and wherein in the execution of said program, the system controller signals a first of the stimulant target units to illuminate the corresponding light source to stimulate the user, the first stimulant target unit, in a first mode of operation, registering actuation thereof by the user in reaction to the illumination when the user brings a body part or other object to within a selected distance of the corresponding proximity sensor without contacting the first stimulant target unit, the first stimulant target unit thereafter activating the corresponding feedback means to alert the user that the first stimulant target unit has been actuated, the first stimulant target unit, in a second mode of operation, registering actuation thereof by the user in reaction to the illumination when the user impacts the housing, the first stimulant target thereafter activating the corresponding feedback means to alert the user that the first stimulant target unit has been actuated;
   and wherein said first stimulant target unit communicates said registering actuation of said first stimulant target unit to the system controller, and said system controller is programmed to signal, in response to communication by said first stimulant target unit of said actuation, a second of the stimulant target units to illuminate the corresponding light source to stimulate the user, the second stimulant target unit, in the first mode of operation, registering actuation thereof by the user in reaction to the illumination when the user brings the body part or other object to within the selected distance of the corresponding proximity sensor without contacting the second stimulant target unit, the second stimulant target thereafter activating the corresponding feedback means to alert the user that the second stimulant target unit has been actuated, the second stimulant target unit, in a second mode of operation, registering actuation thereof by the user in reaction to the illumination when the user impacts the housing, the second stimulant target thereafter activating the corresponding feedback means to alert the user that the second stimulant target unit has been actuated.

2. An exercise training system according to claim 1, wherein the system controller is programmable via a learning mode in which the user actuates various stimulants target units in a sequence that is recorded by the system controller for subsequent playback.

3. An exercise training system according to claim 2, wherein the user selects the proximity distance required to actuate the stimulant target unit by bringing a body part or other object to the vicinity of the stimulant target unit, the closest distance being recorded as the actuation distance.

4. An exercise training system according to claim 1, wherein the number of stimulant target units constituting the system is dynamically configurable and discoverable upon power up of the system controller.

5. An exercise training system according to claim 1, wherein the stimulant target unit includes a lock member for attaching the stimulant target unit to a support mounting accessory, wherein the lock member is one part of a hook and loop fastener and the support mounting accessory provides the other part of the hook and loop fastener.

6. An exercise training system according to claim 1, wherein the light source includes at least one first LED and at least one second LED, and wherein, in the first mode of operation, the stimulant target unit controller generates the stimulus by illuminating the at least one first LED, and, in the second mode of operation, the stimulant target unit controller generates the stimulus by illuminating the second light source.

7. An exercise training system according to claim 1, wherein each individual stimulant target unit is user selectable as to whether to operate in the first mode of operation or in the second mode of operation independent of any other of the stimulant target units.

8. A stimulant target unit, comprising:
   a housing;
   a stimulation source mounted in the housing, the stimulation source providing stimulus to stimulate a user;
   a proximity sensor mounted in the housing, the proximity sensor providing an output of distance between the stimulant target unit and an external object, wherein the proximity sensor includes an infrared receiver and an infrared emitter;
   feedback means for informing the user that the stimulant target unit has been actuated in response to the stimulus;
   a controller connected to the stimulation source, the proximity sensor, and the feedback means, wherein the controller (i) instructs the stimulation source to generate the stimulus, (ii) registers user reaction to the stimulation in bringing a body part or other object to within a selected distance of the proximity sensor, and (iii) thereafter activates the feedback means to alert the user that the stimulant target unit has been actuated;
   wherein the selected proximity distance required to actuate the stimulant target unit is user programmable,
   a controller connected to the stimulation source, the proximity sensor, and the feedback means, wherein the controller is operable in a sunny mode in which the controller is programmed to (i) instruct the stimulation source to generate the stimulus,
(ii) in a first time period, detect a first level of infrared light emitted by the sun, in a second time period, during which the infrared emitter is on and an object blocks out some infrared light emitted by the sun, the controller detects a second level of infrared light that is lower than the first level of infrared light, and in a third time period, during which the infrared emitter is off and the object blocks out some infrared light emitted by the sun, the controller detects a third level of infrared light that is lower than the second level of infrared light, wherein, upon detecting the first, second and third levels of infrared light in the sunny mode, the controller registers user reaction to the stimulation in bringing a body part or other object to within a selected distance of the proximity sensor, and
(iii) thereafter activates the feedback means to alert the user that the stimulant target unit has been actuated.

9. A stimulant target unit according to claim 8, wherein the controller is operable in a non-sunny mode in which the controller is programmed to (i) instruct the stimulation source to generate the stimulus,
(ii) in a first time period, detect a first level of infrared light emitted by the sun, with the infrared emitter turned off, in a second time period, during which the infrared emitter is on and an object blocks out some infrared light emitted by the sun, the controller detects a second level of infrared, during which the infrared emitter is off and the object blocks out some infrared light emitted by the sun, the controller detects a third level of infrared light that is lower than the second level of infrared light, wherein, upon detecting the first, second and third levels of infrared light in the sunny mode, the controller registers user reaction to the stimulation in bringing a body part or other object to within a selected distance of the proximity sensor, and
(iii) thereafter activates the feedback means to alert the user that the stimulant target unit has been actuated.

\* \* \* \* \*